US009909138B2

(12) United States Patent
Deslattes Mays et al.

(10) Patent No.: US 9,909,138 B2
(45) Date of Patent: Mar. 6, 2018

(54) DROUGHT RESISTANCE IN PLANTS: PECTINESTERASE

(71) Applicant: Keygene N.V., Wageningen (NL)

(72) Inventors: Anne Deslattes Mays, Wageningen (NL); Marieke Helena Adriana Van Hulten, Wageningen (NL); Shital Anilkumar Dixit, Wageningen (NL); Martin De Vos, Wageningen (NL); Jesse David Munkvold, Rockville, MD (US); Matthew Vitabile Dileo, Silver Spring, MD (US)

(73) Assignee: Keygene N.V., Wageningen (NL)

( * ) Notice: Subject to any disclaimer, the term of this patent is extended or adjusted under 35 U.S.C. 154(b) by 82 days.

(21) Appl. No.: 14/377,844

(22) PCT Filed: Feb. 18, 2013

(86) PCT No.: PCT/NL2013/050102
§ 371 (c)(1),
(2) Date: Aug. 8, 2014

(87) PCT Pub. No.: WO2013/122473
PCT Pub. Date: Aug. 22, 2013

(65) Prior Publication Data

US 2016/0010108 A1 Jan. 14, 2016

Related U.S. Application Data

(60) Provisional application No. 61/599,959, filed on Feb. 17, 2012.

(51) Int. Cl.
*C12N 15/82* (2006.01)
*G01N 33/00* (2006.01)

(52) U.S. Cl.
CPC ..... *C12N 15/8273* (2013.01); *C12N 15/8218* (2013.01); *C12Y 301/01011* (2013.01); *G01N 33/0098* (2013.01)

(58) Field of Classification Search
None
See application file for complete search history.

(56) References Cited

U.S. PATENT DOCUMENTS 7,435,874 B2 10/2008 Gebhardt
2004/0031072 A1 2/2004 La Rosa et al.
(Continued)

FOREIGN PATENT DOCUMENTS

EP 1 685 242 B1 4/2011
JP 2015-508649 A 3/2015
(Continued)

OTHER PUBLICATIONS

ABRC. Germplasm SALK_136556C. Published Apr. 12, 2007. pp. 1-2.*
(Continued)

*Primary Examiner* — Ashley K Buran
(74) *Attorney, Agent, or Firm* — Sunit Talapatra; Foley & Lardner LLP

(57) ABSTRACT

The present invention relates to a new method for increasing drought resistance of a plant. The method encompasses the impairment of the expression of a gene or genes in said plant. In comparison to a plant not manipulated to impair the expression of said gene(s), the plants display improved drought resistance. Also provided are plants and plant products that can be obtained by the method according to the invention.

6 Claims, 3 Drawing Sheets

0.60
0.50
0.40
0.30
0.20
0.10
0.00

At5g19730 knock-out + Br81413 transgene
At5g19730 knock-out + Slg24530 transgene
At5g19730 knock-out + Os01g53990_2 transgene
At5g19730 knock-out + Os01g53990_1 transgene
At5g19730 knock-out + At5g19730 transgene
Wildtype
At5g19730 knock-out

(56) References Cited

U.S. PATENT DOCUMENTS

2004/0123343 A1 6/2004 La Rosa et al.
2006/0150283 A1 7/2006 Alexandrov et al.
2007/0266453 A1 11/2007 Anderson
2009/0094717 A1 4/2009 Troukhan et al.
2009/0144850 A1 6/2009 Van Winkle
2010/0212050 A1* 8/2010 Shoseyov .......... C12N 15/8273 800/300
2012/0260373 A1* 10/2012 Apuya .............. C12N 15/8261 800/306

FOREIGN PATENT DOCUMENTS

JP 2015-508650 A 3/2015
WO WO-02/083911 A1 10/2002
WO WO-03/020015 A2 3/2003
WO WO-2004/035798 A2 4/2004
WO WO-2011/038389 A2 3/2011

OTHER PUBLICATIONS

ABRC. Germplasm SALK_136556.27.x. Published Mar. 3, 2003. pp. 1-2.*
ExplorEnz. EC 3.1.1.11. Pectinesterase. 2001. pp. 1.*
Chang et al. Papaya pectinesterase inhibition by sucrose. $24^{th}$ Annual Meeting of the Institute of Food Technologies. May 24-28, 1964. pp. 218-222.*
Tian et al. Pollen-specific pectin methylesterase involved in pollen tube growth. Developmental Biology. 2006. 294: 83-91.*
An et al. Pepper pectin methylesterase inhibitor protein CaPMEI1 is required for antifungal activity, basal disease resistance and abiotic stress tolerance. Planta. 2008. 228:61-78.*
Gray et al. The use of transgenic and naturally occurring mutants to understand and manipulate tomato fruit ripening. Plant, Cell and Environment. 1994. 17:557-571.*
Hong et al. Funcational characterization of pectin methylesterase inhibitor (PMEI) in wheat. Genes Genet. Syst. 2010. 85: 97-106.*
Qu et al. Brassinosteroids regulate pectin methylesterase activity and AtPME41 expression in *Arabidopsis* under chilling stress. Cryobiology. 2011. 63(2): 111-117.*
Lionetti et al. Engineering the cell wall by reducing de-methyl-esterified homogalacturonan improves saccharification of plant tissues for bioconversion. PNAS. 2010. 107(2): 616-621.*
Brenner. Errors in genome annotation. TIG. 1999. 15(4): 132-133.*
Hall et al. Antisense inhibition of pectin esterase gene expression in transgenic tomatoes. The Plant Journal. 1993. 3(1): 121-129.*
Alonso, et al. "Genome-Wide Insertional Mutagenesis of *Arabidopsis thaliana*", Science, Aug. 1, 2003, vol. 301, pp. 653-657.
Cho, et al. "*Arabidopsis* PUB22 and PUB23 Are Homologous U-Box E3 Ubiquitin Ligases That Play Combinatory Roles in Response to Drought Stress", The Plant Cell, Jul. 2008, vol. 20, pp. 1899-1914.
Downes, et al. "The HECT ubiquitin-protein ligase (UPL) family in *Arabidopsis*: UPL3 has a specific role in trichome development", The Plant Journal, 2003, vol. 35, pp. 729-742.
International Search Report in PCT/NL2013/050100 dated Jun. 10, 2013.
International Search Report in PCT/NL2013/050101 dated Jun. 10, 2013.
International Search Report in PCT/NL2013/050102 dated Jun. 12, 2013.
Louvet, et al. "Comprehensive expression profiling of the pectin methylesterase gene family during silique development in *Arabidopsis thaliana*", Planta, 2006, vol. 226, pp. 782-791.
Paterson, et al. "The Sorghum bicolor genome and the diversification of grasses", Nature, Jan. 2009, vol. 457, pp. 551-556.
Qin, et al. "*Arabidopsis* DREB2A-Interacting Proteins Function as Ring E3 Ligases and Negatively Regulate Plant Drought Stress-Responsive Gene Expression", The Plant Cell, Jun. 2008, vol. 20, pp. 1693-1707.
Retrieved from EBI accession No. UNIPROT:C5Z1DO, Sep. 1, 2009, "RecName: Full=Pectinesterase; EC=3.1.1.11;".
Retrieved from EBI accession No. UNIPROT:Q8VYZ3, Mar. 1, 2002, "RecName: Full=Probable pectinesterase 53; Short=PE 53; EC=3.1.1.11; AltName: Full=Pectin methylesterase 53; short-AtPME53; Flags: Precursor;".
"*Arabidopsis thaliana* pectinesterase (AT5G19730)mRNA, complete cds", GenBank Database,Accession No. NM_121978.
Aharoni, et al. "The SHINE Clade of AP2 Domain Transcription Factors Activates Wax Biosynthesis, Alters Cuticle Properties, and Confers Drought Tolerance when Overexpressed in *Arabidopsis*", The Plant Cell, Sep. 2004, vol. 16, pp. 2463-2480.
Bray, "Plant responses to water deficit", Trends in Plant Science, Feb. 1997, vol. 2, No. 2, pp. 48-54.
Cho, et al. "ROS-Mediated ABA Signaling", J. Plant Biol., 2009, vol. 52, pp. 102-113.
Denby, et al. "Engineering drought and salinity tolerance in plants: lessons from genome-wide expression profiling in *Arabidopsis*", TRENDS in Biotechnology, Nov. 2005, vol. 23, No. 11, pp. 547-552.
Devereux, J., et al., A comprehensive set of sequence analysis programs for the VAX, Nucleic Acids Research, 1984, vol. 12, Issue 1, pp. 387-395.
Harb, et al. "Molecular and Physiological Analysis of Drought Stress in *Arabidopsis* Reveals Early Responses Leading to Acclimation in Plant Growth", Plant Physiology, Nov. 2010, vol. 154, pp. 1254-1271.
Karaba, et al. "Improvement of water use efficiency in rice by expression of HARDY, an *Arabidopsis* drought and salt tolerance gene", PNAS, Sep. 2007, vol. 104, No. 39, pp. 15270-1575.
Kasuga et al., "Improving Plant Drought, Salt, and Freezing Tolerance by Gene Transfer of a Single Stress-inducible Transcription Factor," Nature Biotechnology, vol. 17, pp. 287-291 (1999).
Kilian, et al. "The AtGenExpress global stress expression data set: protocols, evaluation and model data analysis of UV-B light, drought and cold stress responses", The Plant Journal, 2007, vol. 50, pp. 347-363.
Kwak, et al. "NADPH oxidase AtrbohD and AtrbohF genes function in ROS-dependent ABA signaling in *Arabidopsis*", The EMBO Journal, 2003, vol. 22, No. 11, pp. 2623-2633.
Kwak, et al. "The Clickable Guard Cell, Version II: Interactive Model of Guard Cell Signal Transduction Mechanisms and Pathways", *Arabidopsis* Book, 2008, vol. 6, e0114, 16 pgs.
Kwak, et al. "The Role of Reactive Oxygen Species in Hormonal Responses", Plant Physiology, Jun. 2006, vol. 141, pp. 323-329.
Lee, et al. "Activation of Glucosidase via Stress-Induced Polymerization Rapidly Increases Active Pools of Abscisic Acid", Cell, Sep. 2006, vol. 126, pp. 1109-1120.
Pennisi, "The Blue Revolution, Drop By Drop, Gene by Gene", Science, Apr. 2008, vol. 320, pp. 171-173.
Serrano, et al. "A glimpse of the mechanisms of ion homeostasis during salt stress", Journal of Experimental Botany, Jun. 1999, vol. 50, Special Issue, pp. 1023-1036.
Sinaki, et al. "The Effects of Water Deficit During Growth Stages of Canola (*Brassica napus* L.)", American-Eurasian J. Agric. & Environ. Sci, 2007, vol. 2, No. 4, pp. 417-422.
Snow, et al. "Evaluation of a System for the Imposition of Plant Water Stress", Plant Physiol, 1985, vol. 77, pp. 602-607.
Swindell, "The Association Among Gene Expression Responses to Nine Abiotic Stress Treatments in *Arabidopsis thaliana*", Genetics, Dec. 2006, vol. 1811-1824.
Wang, et al. "Plant responses to drought, salinity and extreme temperatures: towards genetic engineering for stress tolerance", Planta, 2003, vol. 218, pp. 1-14.
Barbagallo, et al. "Pectin methylesterase, polyphenol oxidase and physicochemical properties of typical long-storage cherry tomatoes cultivated under water stress regime", Journal of Science of food and Agriculture (2008) vol. 88, pp. 389-396.
Camacho-Cristobal, et al. "The expression of several cell wall-related genes in *Arabidopsis* roots is down-regulated under boron deficiency" Environmental and Experimental Botany (2008) vol. 63, pp. 351-358.

(56) References Cited

OTHER PUBLICATIONS

El Refy, et al. "The *Arabidopsis* KAKTUS gene encodes a HECT protein and controls the number of endoreduplication cycles", Mol Gen Genomics (2003), vol. 270, pp. 403-414.
Fagard, et al. "Cell wall mutants" Plant Physiology and Biochemistry (Jan. 2000) vol. 38,(1/2), pp. 15-25.
Hyun An, et al. "Pepper pectin methylesterase inhibitor protein CaPMEI1 is required for antifungal activity, basal disease resistance and abiotic stress tolerance", Planta (2008) vol. 228, pp. 61-78.
International Search Report & Written Opinion in NL Appln No. 2006007 dated Aug. 18, 2011.
Perazza, et al. "Trichome Cell Growth in *Arabidopsis thaliana* Can Be Depressed by Mutations in at Least Five Genes", Genetics (May 1999), vol. 152, pp. 461-476.
Search Report in NL Appln No. 2006006 dated Aug. 17, 2011.
Seymour, et al. "Down-regulation of two non-homologous endogenous tomato genes with a single chimaeric sense gene construct", Database Accession No. PREV199497005095 (1993).
Speulman, et al. "Target selected insertional mutagenesis on chromosome IV of *Arabidopsis* using the En-I transposon system", Journal of Biotechnology (2000), vol. 78, pbs 301-312.
Tian, et al. "Pollen-specific pectin methylesterase involved in pollen tube growth", Developmental Biology (2006) vol. 294, pp. 83-91.
Yamada, et al. "*Arabidopsis thaliana* putative pectin methylesterase (At5g19730) mRNA, complete cds", Database acession No. AY065431 (Dec. 13, 2001).
Zhi-Biao, et al. "Analysis of two antisense transgenes inhibiting expression of their endogenous genes in transgenic tomatoes", Database Accession No. PREV199699184897 (1996).
Coates et al., "Armadillo repeat proteins: versatile regulators of plant development and signaling", Plant Cell Monographs, 2007, vol. 10. pp. 299-314.
Gul et al., "Metazoan evolution of the armadillo repeat superfamily", Cell. Mol. Life Sci., 2017, vol. 74, pp. 525-541.
Mudgil et al., "A large complement of the predicted *Arabidopsis* ARM repeat proteins are members of the U-Box E3 ubiquitin ligase family", Plant Physiology, Jan. 2004, vol. 134, pp. 59-66.
Notice of Reasons for Rejection issued in co-pending Japanese Application No. 2014-557587, dated Jan. 31, 2017, with English translation.
Notice of Reasons for Rejection issued in co-pending Japanese Application No. 2014-557588, dated Jan. 31, 2017, with English translation.
Rotin et al., "Physiological functions of the HECT family of ubiquitin ligases", Nature Reviews Molecular Cell Biology, 2009, vol. 10, pp. 398-409.

* cited by examiner

Wild-type At5g19730 KO

SEQUENCE LISTING

<160> NUMBER OF SEQ ID NOS: 10

<210> SEQ ID NO 1
<211> LENGTH: 1149
<212> TYPE: DNA
<213> ORGANISM: Arabidopsis thaliana

<400> SEQUENCE: 1
atgcccaaac tcaattcaac ccaagctccc aatttattcc ttctccttct cgttatcctt 60
ctttgttcaa cgcaaacaca atgccacacc aaaggtctcc gattacgacc aagaaaccag 120
aagaatatga acacgacgag tgatcggaca caaaacccgg aagatgagtt catgaaatgg 180
gtgagattcg ttggaagcct taaacactca gtgttcaagg cagccaagaa caaactcttc 240
ccttcttata cattaactgt ccacaagaaa tccaataaag gtgacttcac taaaatccaa 300
gacgccattg attctctccc tctcatcaac tttgttcgtg tcgtcatcaa agttcatgcc 360
ggagtttaca aggagaaggt gagcataccc ccactgaagg catttataac aatagaagga 420
gaaggagcag agaagacaac agtggaatgg ggagacacag cacaaacccc tgactcaaaa 480
ggcaacccca tgggcactta caactcggcc tcgttcgcgg tcaactctcc tttctttgtc 540
gctaagaata tcacattcag gaacacgacc ccagtcccct tgcccggtgc agttggtaaa 600
caggcggtag cattgagggt gtcggcagac aatgccgcgt tttttgggtg tagaatgctt 660
ggtgctcaag acactctcta tgaccatttg ggaagacatt attacaaaga ttgttacatt 720
gagggatcag tggacttcat ctttggaaat gccctttctc tttatgaagg gtgccacgtg 780
catgcgatag cggataagct aggagcagtg acggcacagg ggaggagcag tgttctagag 840
gacaccggat tctcgttcgt aaagtgtaag gtgacaggga caggggtttt gtatcttggg 900
agggcatggg gtcccttctc aagagtcgtt tttgcttaca cttacatgga caacatcatc 960
ctccctagag gctggtacaa ttggggagac ccttcccgtg agatgacggt gttctatggg 1020
cagtacaagt gcacgggagc aggagcaaac tatggaggga gggtggcttg ggcaagagag 1080
ctcaccgacg aagaagctaa gccttttctt tctcttacct ttatcgacgg ctctgaatgg 1140
atcaaactc 1149

<210> SEQ ID NO 2
<211> LENGTH: 383
<212> TYPE: PRT
<213> ORGANISM: Arabidopsis thaliana

<400> SEQUENCE: 2

Met Pro Lys Leu Asn Ser Thr Gln Ala Pro Asn Leu Phe Leu Leu Leu
1 5 10 15

Leu Val Ile Leu Leu Cys Ser Thr Gln Thr Gln Cys His Thr Lys Gly
20 25 30

Leu Arg Leu Arg Pro Arg Asn Gln Lys Asn Met Asn Thr Thr Ser Asp
35 40 45

```
Arg Thr Gln Asn Pro Glu Asp Glu Phe Met Lys Trp Val Arg Phe Val
    50                  55                  60

Gly Ser Leu Lys His Ser Val Phe Lys Ala Ala Lys Asn Lys Leu Phe
65                  70                  75                  80

Pro Ser Tyr Thr Leu Thr Val His Lys Lys Ser Asn Lys Gly Asp Phe
                85                  90                  95

Thr Lys Ile Gln Asp Ala Ile Asp Ser Leu Pro Leu Ile Asn Phe Val
            100                 105                 110

Arg Val Val Ile Lys Val His Ala Gly Val Tyr Lys Glu Lys Val Ser
        115                 120                 125

Ile Pro Pro Leu Lys Ala Phe Ile Thr Ile Glu Gly Glu Gly Ala Glu
    130                 135                 140

Lys Thr Thr Val Glu Trp Gly Asp Thr Ala Gln Thr Pro Asp Ser Lys
145                 150                 155                 160

Gly Asn Pro Met Gly Thr Tyr Asn Ser Ala Ser Phe Ala Val Asn Ser
                165                 170                 175

Pro Phe Phe Val Ala Lys Asn Ile Thr Phe Arg Asn Thr Thr Pro Val
            180                 185                 190

Pro Leu Pro Gly Ala Val Gly Lys Gln Ala Val Ala Leu Arg Val Ser
        195                 200                 205

Ala Asp Asn Ala Ala Phe Phe Gly Cys Arg Met Leu Gly Ala Gln Asp
    210                 215                 220

Thr Leu Tyr Asp His Leu Gly Arg His Tyr Tyr Lys Asp Cys Tyr Ile
225                 230                 235                 240

Glu Gly Ser Val Asp Phe Ile Phe Gly Asn Ala Leu Ser Leu Tyr Glu
                245                 250                 255

Gly Cys His Val His Ala Ile Ala Asp Lys Leu Gly Ala Val Thr Ala
            260                 265                 270

Gln Gly Arg Ser Ser Val Leu Glu Asp Thr Gly Phe Ser Phe Val Lys
        275                 280                 285

Cys Lys Val Thr Gly Thr Gly Val Leu Tyr Leu Gly Arg Ala Trp Gly
    290                 295                 300

Pro Phe Ser Arg Val Val Phe Ala Tyr Thr Tyr Met Asp Asn Ile Ile
305                 310                 315                 320

Leu Pro Arg Gly Trp Tyr Asn Trp Gly Asp Pro Ser Arg Glu Met Thr
                325                 330                 335

Val Phe Tyr Gly Gln Tyr Lys Cys Thr Gly Ala Gly Ala Asn Tyr Gly
            340                 345                 350

Gly Arg Val Ala Trp Ala Arg Glu Leu Thr Asp Glu Glu Ala Lys Pro
        355                 360                 365

Phe Leu Ser Leu Thr Phe Ile Asp Gly Ser Glu Trp Ile Lys Leu
    370                 375                 380

<210> SEQ ID NO 3
<211> LENGTH: 1149
<212> TYPE: DNA
<213> ORGANISM: Brassica rapa

<400> SEQUENCE: 3

atgccccaat tcagttcatc ccaagctccc attttaatcc tccccgttct cattatactt      60

ctgtgttcaa cgcaaacaca atgccacacc aaagggctac gattgcgacc aagaaaccag     120

aagattgtga actctacgag tcagacacaa aaccctgaag aggaattctt gaaatgggtt     180

agatacgttg ggagccttaa gcacacggtg ttcaaggcag ccaagaacaa actcttcgct     240
```

```
tcgtatacac tcactgttca taagaaacac aacaaaggtg acttcactaa aatccaagac    300

gccatagatt ctctgcctct catcaacctc gttcgtgtcg tcatcaaagt tcatgctgga    360

gtttacaagg aaaaggtgaa catacctcca atgaaggcat tcataacaat agaaggagaa    420

ggagcagata aaacaatagt gcaatgggga gacacagcac aaacacatga cccaaaaggc    480

aatcccatgg gcaccttcaa ctctgcctct tttgccgtca actctccttt ctttgtcgcg    540

aagaacatca ctttcaagaa cacgacacca gtccccttgc caggcgcggt tggaaaacaa    600

gcggtggcat tgagagtgtc agccgacaat gctgcttttt tcgggtgtaa aatgcttggt    660

gctcaagaca ctctctatga ccatttggga agacattatt acaaagactg ttacattgaa    720

ggatccgttg atttcatctt tggcaatgcc ctttctctct acgaggggtg tcacgtgcac    780

gcaatagcgg ataagctagg agcagtgacg gcgcaaggaa ggagcagtgt gctagaggac    840

acaggattct cgttcgtgaa gtgtaaggtg acagggacag gagtattgta ccttgggagg    900

gcatggggtc ccttctcaag agtcgtattt gcttacacct atatggacaa catcatcctc    960

cctaaaggct ggtacaattg ggcgaccct tcacgcgaga tgacggtgtt ctatgggcag    1020

tacaagtgca cgggagcagg agcaaactat gcagggaggg tggcttgggc aagagagctc    1080

accgacgaag aagctaagcc ttttatatct cttaccttca tcgacggttc tgaatggatc    1140

agactctaa                                                            1149
```

<210> SEQ ID NO 4
<211> LENGTH: 382
<212> TYPE: PRT
<213> ORGANISM: Brassica rapa

<400> SEQUENCE: 4

```
Met Pro Gln Phe Ser Ser Ser Gln Ala Pro Ile Leu Ile Leu Pro Val
1               5                   10                  15

Leu Ile Ile Leu Leu Cys Ser Thr Gln Thr Gln Cys His Thr Lys Gly
            20                  25                  30

Leu Arg Leu Arg Pro Arg Asn Gln Lys Ile Val Asn Ser Thr Ser Gln
        35                  40                  45

Thr Gln Asn Pro Glu Glu Glu Phe Leu Lys Trp Val Arg Tyr Val Gly
    50                  55                  60

Ser Leu Lys His Thr Val Phe Lys Ala Ala Lys Asn Lys Leu Phe Ala
65                  70                  75                  80

Ser Tyr Thr Leu Thr Val His Lys Lys His Asn Lys Gly Asp Phe Thr
                85                  90                  95

Lys Ile Gln Asp Ala Ile Asp Ser Leu Pro Leu Ile Asn Leu Val Arg
            100                 105                 110

Val Val Ile Lys Val His Ala Gly Val Tyr Lys Glu Lys Val Asn Ile
        115                 120                 125

Pro Pro Met Lys Ala Phe Ile Thr Ile Glu Gly Glu Gly Ala Asp Lys
    130                 135                 140

Thr Ile Val Gln Trp Gly Asp Thr Ala Gln Thr His Asp Pro Lys Gly
145                 150                 155                 160

Asn Pro Met Gly Thr Phe Asn Ser Ala Ser Phe Ala Val Asn Ser Pro
                165                 170                 175

Phe Phe Val Ala Lys Asn Ile Thr Phe Lys Asn Thr Thr Pro Val Pro
            180                 185                 190

Leu Pro Gly Ala Val Gly Lys Gln Ala Val Ala Leu Arg Val Ser Ala
        195                 200                 205
```

```
Asp Asn Ala Ala Phe Phe Gly Cys Lys Met Leu Gly Ala Gln Asp Thr
    210                 215                 220

Leu Tyr Asp His Leu Gly Arg His Tyr Tyr Lys Asp Cys Tyr Ile Glu
225                 230                 235                 240

Gly Ser Val Asp Phe Ile Phe Gly Asn Ala Leu Ser Leu Tyr Glu Gly
                245                 250                 255

Cys His Val His Ala Ile Ala Asp Lys Leu Gly Ala Val Thr Ala Gln
            260                 265                 270

Gly Arg Ser Ser Val Leu Glu Asp Thr Gly Phe Ser Phe Val Lys Cys
        275                 280                 285

Lys Val Thr Gly Thr Gly Val Leu Tyr Leu Gly Arg Ala Trp Gly Pro
    290                 295                 300

Phe Ser Arg Val Val Phe Ala Tyr Thr Tyr Met Asp Asn Ile Ile Leu
305                 310                 315                 320

Pro Lys Gly Trp Tyr Asn Trp Gly Asp Pro Ser Arg Glu Met Thr Val
                325                 330                 335

Phe Tyr Gly Gln Tyr Lys Cys Thr Gly Ala Gly Ala Asn Tyr Ala Gly
            340                 345                 350

Arg Val Ala Trp Ala Arg Glu Leu Thr Asp Glu Glu Ala Lys Pro Phe
        355                 360                 365

Ile Ser Leu Thr Phe Ile Asp Gly Ser Glu Trp Ile Arg Leu
    370                 375                 380


<210> SEQ ID NO 5
<211> LENGTH: 1065
<212> TYPE: DNA
<213> ORGANISM: Solanum lycopersicum

<400> SEQUENCE: 5

atgttaatgt tgtttactat tagcacaagt agtgctagaa gggataatac attgaaggtg      60

gctaatgaag aaaaagacta cttgaattgg attcatcgca tgagttctcg caatcattct     120

gttttccaag aagctaagaa caaattagag ccttgtaaat ttattaaggt gaataaaaac     180

ccgaaattcg gagattttac tacggttcag aaggctattg attcaatccc aatagtcaat     240

tcgtgtcgag tggttatttc tgttagtcct ggaacttaca gggaaaagat tgaaattcca     300

gcaacaatgg cttacattac cctggaaggt gctgcttcac ataaaaacaac tatcaaatgg     360

gatgacactg cagataggac aggaaaaagt ggccaaccaa tgggaactta tggttccgca     420

acttttgctg ttaattcccc ctatttcatt gccaaaaaca tcacctttaa gaatgtagca     480

ccaccaccac catcaggggc actaggaaag caagcggtgg cattaagaat atcggcagac     540

acagcggcgt tcataaattg caagttcatt ggagcacagg acacactgta tgatcacagg     600

ggcaggcact atttcaagaa ctgttatatt caaggttctg tagattttat atttggtgat     660

gggctctccc tttatgagaa ttgtcattta cgtgcaaaaa caaaaagcta tggggcattg     720

acagcccaga agagggagag tttactggag gaaactggat tctcttttct caattgcaaa     780

gttactggat ctggtgctct ttacttgggc agggcttggg gtactttctc tagggtcgta     840

tttgcttaca cttatatgga taaaattatc acatcaaagg gatggtatga ctggggagat     900

aagaacaggc atatgacggt attttttggg caattcaagt gttcaggacc aggggcagac     960

catggtgaaa gggtgaaatg gtccagggag ctcactgaac aagaagctaa accgtttatc    1020

tcactcagtt tcatagatgg tcatgaatgg ttactccata tttga                    1065


<210> SEQ ID NO 6
```

```
<211> LENGTH: 354
<212> TYPE: PRT
<213> ORGANISM: Solanum lycopersicum

<400> SEQUENCE: 6

Met Leu Met Leu Phe Thr Ile Ser Thr Ser Ser Ala Arg Arg Asp Asn
1               5                   10                  15

Thr Leu Lys Val Ala Asn Glu Glu Lys Asp Tyr Leu Asn Trp Ile His
            20                  25                  30

Arg Met Ser Ser Arg Asn His Ser Val Phe Gln Glu Ala Lys Asn Lys
        35                  40                  45

Leu Glu Pro Cys Lys Phe Ile Lys Val Asn Lys Asn Pro Lys Phe Gly
    50                  55                  60

Asp Phe Thr Thr Val Gln Lys Ala Ile Asp Ser Ile Pro Ile Val Asn
65                  70                  75                  80

Ser Cys Arg Val Val Ile Ser Val Ser Pro Gly Thr Tyr Arg Glu Lys
                85                  90                  95

Ile Glu Ile Pro Ala Thr Met Ala Tyr Ile Thr Leu Glu Gly Ala Ala
            100                 105                 110

Ser His Lys Thr Thr Ile Lys Trp Asp Asp Thr Ala Asp Arg Thr Gly
        115                 120                 125

Lys Ser Gly Gln Pro Met Gly Thr Tyr Gly Ser Ala Thr Phe Ala Val
    130                 135                 140

Asn Ser Pro Tyr Phe Ile Ala Lys Asn Ile Thr Phe Lys Asn Val Ala
145                 150                 155                 160

Pro Pro Pro Pro Ser Gly Ala Leu Gly Lys Gln Ala Val Ala Leu Arg
                165                 170                 175

Ile Ser Ala Asp Thr Ala Ala Phe Ile Asn Cys Lys Phe Ile Gly Ala
            180                 185                 190

Gln Asp Thr Leu Tyr Asp His Arg Gly Arg His Tyr Phe Lys Asn Cys
        195                 200                 205

Tyr Ile Gln Gly Ser Val Asp Phe Ile Phe Gly Asp Gly Leu Ser Leu
    210                 215                 220

Tyr Glu Asn Cys His Leu Arg Ala Lys Thr Lys Ser Tyr Gly Ala Leu
225                 230                 235                 240

Thr Ala Gln Lys Arg Glu Ser Leu Leu Glu Glu Thr Gly Phe Ser Phe
                245                 250                 255

Leu Asn Cys Lys Val Thr Gly Ser Gly Ala Leu Tyr Leu Gly Arg Ala
            260                 265                 270

Trp Gly Thr Phe Ser Arg Val Val Phe Ala Tyr Thr Tyr Met Asp Lys
        275                 280                 285

Ile Ile Thr Ser Lys Gly Trp Tyr Asp Trp Gly Asp Lys Asn Arg His
    290                 295                 300

Met Thr Val Phe Phe Gly Gln Phe Lys Cys Ser Gly Pro Gly Ala Asp
305                 310                 315                 320

His Gly Glu Arg Val Lys Trp Ser Arg Glu Leu Thr Glu Gln Glu Ala
                325                 330                 335

Lys Pro Phe Ile Ser Leu Ser Phe Ile Asp Gly His Glu Trp Leu Leu
            340                 345                 350

His Ile


<210> SEQ ID NO 7
<211> LENGTH: 1155
<212> TYPE: DNA
<213> ORGANISM: Oryza sativa
```

<400> SEQUENCE: 7

```
atggccgtgg cgcccgtccg gctcgtggcg tgcattgtcg ccctggccgc cgtggcgccg      60
ggcggagtgg cggggcacac acggggcgtg cggccaggga gggcggcggg gaagcagcag     120
ccgtcgttcc cggagaacgc gacgcgggtg gaggcgatcg agcggcagtt catggagtgg     180
gtacggtaca tgggcgggct ggagcacagc acggtccacc acgcgctcgc ccgggcgttc     240
ccctcctact cgctcgtcgt cgacaagaac ccggcgttcg gcgacttcac caccatccag     300
gccgccgtcg actcgctccc gatcatcaac ctcgtccgcg tcgtcatcaa ggtcaacgcc     360
ggcacctaca cggagaaggt gaacatatcg ccgatgcgcg cgttcatcac cctcgagggc     420
gccggcgccg acaagacgat cgtgcagtgg ggtgacaccg cggacagtcc gtccggccgg     480
gcgggacggc cgctcggcac atacagctcc gcgtcgttcg ccgtgaacgc gcagtacttc     540
ctcgccagga acatcacttt caagaacacg tcgccggtgc cgaagccggg ggcgtcgggg     600
aagcaggcgg tggcgctgcg ggtgtcggcg gacaacgcgg cgttcgtggg gtgcaggttc     660
ctgggcgcgc aggacacgct gtacgatcac tcgggccggc actactacaa ggaatgctac     720
atcgaaggct ccgtggattt catctttggc aatgcgctct ctctgtttga ggattgccac     780
gtgcatgcga tcgcgcggga ctacggcgcg ctgacagcgc agaaccggca gagcatgctg     840
gaggacacgg ggttctcgtt cgtcaactgc cgggtgacgg gatccggcgc gctctacctc     900
ggccgcgcct ggggcacctt ctcccgcgtc gtcttcgcct acacctacat ggacgacatc     960
atcatccccc gtggctggta caactggggc gaccccaacc gcgagctgac ggtgttctac    1020
gggcagtaca agtgcacggg ccccggcgcg agcttctccg gcagggtgtc gtggtcacgc    1080
gagctcaccg acgaggaggc caagcccttc atctcgctca ccttcatcga cggcacggaa    1140
tgggtcaggt tgtga                                                     1155
```

<210> SEQ ID NO 8
<211> LENGTH: 384
<212> TYPE: PRT
<213> ORGANISM: Oryza sativa

<400> SEQUENCE: 8

```
Met Ala Val Ala Pro Val Arg Leu Val Ala Cys Ile Val Ala Leu Ala
1               5                   10                  15

Ala Val Ala Pro Gly Gly Val Ala Gly His Thr Arg Gly Val Arg Pro
            20                  25                  30

Gly Arg Ala Ala Gly Lys Gln Gln Pro Ser Phe Pro Glu Asn Ala Thr
        35                  40                  45

Arg Val Glu Ala Ile Glu Arg Gln Phe Met Glu Trp Val Arg Tyr Met
    50                  55                  60

Gly Gly Leu Glu His Ser Thr Val His His Ala Leu Ala Arg Ala Phe
65                  70                  75                  80

Pro Ser Tyr Ser Leu Val Val Asp Lys Asn Pro Ala Phe Gly Asp Phe
                85                  90                  95

Thr Thr Ile Gln Ala Ala Val Asp Ser Leu Pro Ile Ile Asn Leu Val
            100                 105                 110

Arg Val Val Ile Lys Val Asn Ala Gly Thr Tyr Thr Glu Lys Val Asn
        115                 120                 125

Ile Ser Pro Met Arg Ala Phe Ile Thr Leu Glu Gly Ala Gly Ala Asp
    130                 135                 140

Lys Thr Ile Val Gln Trp Gly Asp Thr Ala Asp Ser Pro Ser Gly Arg
```

```
145                 150                 155                 160

Ala Gly Arg Pro Leu Gly Thr Tyr Ser Ser Ala Ser Phe Ala Val Asn
                165                 170                 175

Ala Gln Tyr Phe Leu Ala Arg Asn Ile Thr Phe Lys Asn Thr Ser Pro
            180                 185                 190

Val Pro Lys Pro Gly Ala Ser Gly Lys Gln Ala Val Ala Leu Arg Val
        195                 200                 205

Ser Ala Asp Asn Ala Ala Phe Val Gly Cys Arg Phe Leu Gly Ala Gln
    210                 215                 220

Asp Thr Leu Tyr Asp His Ser Gly Arg His Tyr Tyr Lys Glu Cys Tyr
225                 230                 235                 240

Ile Glu Gly Ser Val Asp Phe Ile Phe Gly Asn Ala Leu Ser Leu Phe
                245                 250                 255

Glu Asp Cys His Val His Ala Ile Ala Arg Asp Tyr Gly Ala Leu Thr
            260                 265                 270

Ala Gln Asn Arg Gln Ser Met Leu Glu Asp Thr Gly Phe Ser Phe Val
        275                 280                 285

Asn Cys Arg Val Thr Gly Ser Gly Ala Leu Tyr Leu Gly Arg Ala Trp
    290                 295                 300

Gly Thr Phe Ser Arg Val Val Phe Ala Tyr Thr Tyr Met Asp Asp Ile
305                 310                 315                 320

Ile Ile Pro Arg Gly Trp Tyr Asn Trp Gly Asp Pro Asn Arg Glu Leu
                325                 330                 335

Thr Val Phe Tyr Gly Gln Tyr Lys Cys Thr Gly Pro Gly Ala Ser Phe
            340                 345                 350

Ser Gly Arg Val Ser Trp Ser Arg Glu Leu Thr Asp Glu Glu Ala Lys
        355                 360                 365

Pro Phe Ile Ser Leu Thr Phe Ile Asp Gly Thr Glu Trp Val Arg Leu
    370                 375                 380


<210> SEQ ID NO 9
<211> LENGTH: 1011
<212> TYPE: DNA
<213> ORGANISM: Oryza sativa

<400> SEQUENCE: 9

atggccgtgg cgcccgtccg gctcgtggcg tgcattgtcg ccctggccgc cgtggcgccg      60

ggcggagtgg cggggcacac acggggcgtg cggccaggga gggcggcggg gaagcagcag     120

ccgtcgttcc cggagaacgc gacgcgggtg gaggcgatcg agcggcagtt catggagtgg     180

gtacggtaca tgggcgggct ggagcacagc acggtccacc acgcgctcgc ccgggcgttc     240

ccctcctact cgctcgtcgt cgacaagaac ccggcgttcg gcgacttcac caccatccag     300

gccgccgtcg actcgctccc gatcatcaac ctcgtccgcg tcgtcatcaa ggtcaacgcc     360

ggcacctaca cggagaaggt gaacatatcg ccgatgcgcg cgttcatcac cctcgagggc     420

gccggcgccg acaagacgat cgtgcagtgg ggtgacaccg cggacagtcc gtccggccgg     480

gcgggacggc cgctcggcac atacagctcc gcgtcgttcg ccgtgaacgc gcagtacttc     540

ctcgccagga acatcacttt caagaacacg tcgccggtgc cgaagccggg ggcgtcgggg     600

aagcaggcgg tggcgctgcg ggtgtcggcg gacaacgcgg cgttcgtggg gtgcaggttc     660

ctgggcgcgc aggacacgct gtacgatcac tcgggccggc actactacaa ggaatgctac     720

atcgaaggct ccgtggattt catctttggc aatgcgctct ctctgtttga ggattgccac     780

gtgcatgcga tcgcgcggga ctacggcgcg ctgacagcgc agaaccggca gagcatgctg     840
```

```
gaggacacgg ggttctcgtt cgtcaactgc cgggtgacgg gatccggcgc gctctacctc    900

ggccgcgcct ggggcacctt ctcccgcgtc gtcttcgcct acacctacat ggacgacatc    960

atcatccccc gtggctggta caactggggc gaccccaacc gcgagctgta a            1011


<210> SEQ ID NO 10
<211> LENGTH: 336
<212> TYPE: PRT
<213> ORGANISM: Oryza sativa

<400> SEQUENCE: 10

Met Ala Val Ala Pro Val Arg Leu Val Ala Cys Ile Val Ala Leu Ala
1               5                   10                  15

Ala Val Ala Pro Gly Gly Val Ala Gly His Thr Arg Gly Val Arg Pro
            20                  25                  30

Gly Arg Ala Ala Gly Lys Gln Gln Pro Ser Phe Pro Glu Asn Ala Thr
        35                  40                  45

Arg Val Glu Ala Ile Glu Arg Gln Phe Met Glu Trp Val Arg Tyr Met
    50                  55                  60

Gly Gly Leu Glu His Ser Thr Val His His Ala Leu Ala Arg Ala Phe
65                  70                  75                  80

Pro Ser Tyr Ser Leu Val Val Asp Lys Asn Pro Ala Phe Gly Asp Phe
                85                  90                  95

Thr Thr Ile Gln Ala Ala Val Asp Ser Leu Pro Ile Ile Asn Leu Val
            100                 105                 110

Arg Val Val Ile Lys Val Asn Ala Gly Thr Tyr Thr Glu Lys Val Asn
        115                 120                 125

Ile Ser Pro Met Arg Ala Phe Ile Thr Leu Glu Gly Ala Gly Ala Asp
    130                 135                 140

Lys Thr Ile Val Gln Trp Gly Asp Thr Ala Asp Ser Pro Ser Gly Arg
145                 150                 155                 160

Ala Gly Arg Pro Leu Gly Thr Tyr Ser Ser Ala Ser Phe Ala Val Asn
                165                 170                 175

Ala Gln Tyr Phe Leu Ala Arg Asn Ile Thr Phe Lys Asn Thr Ser Pro
            180                 185                 190

Val Pro Lys Pro Gly Ala Ser Gly Lys Gln Ala Val Ala Leu Arg Val
        195                 200                 205

Ser Ala Asp Asn Ala Ala Phe Val Gly Cys Arg Phe Leu Gly Ala Gln
    210                 215                 220

Asp Thr Leu Tyr Asp His Ser Gly Arg His Tyr Tyr Lys Glu Cys Tyr
225                 230                 235                 240

Ile Glu Gly Ser Val Asp Phe Ile Phe Gly Asn Ala Leu Ser Leu Phe
                245                 250                 255

Glu Asp Cys His Val His Ala Ile Ala Arg Asp Tyr Gly Ala Leu Thr
            260                 265                 270

Ala Gln Asn Arg Gln Ser Met Leu Glu Asp Thr Gly Phe Ser Phe Val
        275                 280                 285

Asn Cys Arg Val Thr Gly Ser Gly Ala Leu Tyr Leu Gly Arg Ala Trp
    290                 295                 300

Gly Thr Phe Ser Arg Val Val Phe Ala Tyr Thr Tyr Met Asp Asp Ile
305                 310                 315                 320

Ile Ile Pro Arg Gly Trp Tyr Asn Trp Gly Asp Pro Asn Arg Glu Leu
                325                 330                 335
```

DROUGHT RESISTANCE IN PLANTS: PECTINESTERASE

CROSS REFERENCE TO RELATED APPLICATIONS

The present application is a National Stage of International Application No. PCT/NL2013/050102 filed on Feb. 18, 2013, which claims the benefit of U.S. Application No. 61/599,959 filed on Feb. 17, 2012, the entire disclosures of which are incorporated herein by reference.

TECHNICAL FIELD

The present invention relates to a method for increasing drought resistance of a plant. The method encompasses the impairment of the expression of a gene or genes in said plant. In comparison to a plant not manipulated to impair the expression of said gene(s), the plant displays improved drought resistance. Also provided are plants and plant products that can be obtained by the method according to the invention.

BACKGROUND OF THE INVENTION

Abiotic stresses, such as drought, salinity, extreme temperatures, chemical toxicity and oxidative stress are threats to agriculture and it is the primary cause of crop loss worldwide (Wang et al. (2003) Planta 218(1) 1-14).

In the art, several reports are available dealing with the biochemical, molecular and genetic background of abiotic stress (Wang et al. (2003) Planta 218(1) 1-14 or Kilian et al (2007) Plant J 50(2) 347-363). Plant modification to deal with abiotic stress is often based on manipulation of genes that protect and maintain the function and structure of cellular components. However, due to the genetically complex responses to abiotic stress conditions, such plants appear to be more difficult to control and engineer. Wang (Wang et al. (2003) Planta 218(1) 1-14), inter alia, mentions that one of the strategies of engineering relies on the use of one or several genes that are either involved in signalling and regulatory pathways, or that encode enzymes present in pathways leading to the synthesis of functional and structural protectants, such as osmolytes and antioxidants, or that encode stress-tolerance-conferring proteins.

Although improvements in providing abiotic stress tolerant plants have been reported, the nature of the genetically complex mechanisms underlying it provides a constant need for further improvement in this field. For example, it has been reported that genetically transformed drought tolerant plants generally may exhibit slower growth and reduced biomass (Serrano et al (1999) J Exp Bot 50:1023-1036) due to an imbalance in development and physiology, thus having significant fitness cost in comparison with plants that are not transformed (Kasuga et al. (1999) Nature Biot. Vol. 17; Danby and Gehring (2005) Trends in Biot. Vol. 23 No. 11).

Several biotechnological approaches are proposed in order to obtain plants growing under stress conditions. Plants with increased resistance to salt stress are for example disclosed in WO03/020015. This document discloses transgenic plants that are resistant to salt stress by utilizing 9-cis-epoxycarotenoid dioxygenase nucleic acids and polypeptides.

Plants with increased drought tolerance are disclosed in, for example, US 2009/0144850, US 2007/0266453, and WO 2002/083911. US2009/0144850 describes a plant displaying a drought tolerance phenotype due to altered expression of a DR02 nucleic acid. US 2007/0266453 describes a plant displaying a drought tolerance phenotype due to altered expression of a DR03 nucleic acid and WO 2002/083911 describes a plant having an increased tolerance to drought stress due to a reduced activity of an ABC transporter which is expressed in guard cells. Another example is the work by Kasuga and co-authors (1999), who describe that overexpression of cDNA encoding DREB1A in transgenic plants activated the expression of many stress tolerance genes under normal growing conditions and resulted in improved tolerance to drought, salt loading, and freezing. However, the expression of DREB1A also resulted in severe growth retardation under normal growing conditions (Kasuga (1999) Nat Biotechnol 17(3) 287-291). There remains a need for new, alternative and/or additional methodology for increasing resistance to abiotic stress, in particular abiotic stress like drought.

It is an object of the current invention to provide for new methods to increase drought resistance in a plant. With such plant it is, for example, possible to produce more biomass and/or more crop and plant product derived thereof if grown under conditions of low water availability/drought in comparison with plants not subjected to the method according to the invention.

SUMMARY OF THE INVENTION

In a first aspect, the present invention provides a method for producing a plant having improved drought resistance compared to a control plant, comprising the step of impairing expression of functional pectinesterase protein in a plant, plant protoplast or plant cell, wherein said functional pectinesterase protein comprises an amino acid sequence having at least 55% identity with the amino acid sequence of SEQ ID. No. 2, and optionally regenerating said plant.

The functional pectinesterase protein may be a protein that, when expressed in an *Arabidopsis thaliana* T-DNA insertion line having a disrupted endogenous pectinesterase gene, results in a plant with an impaired drought resistance compared to the drought resistance of said *Arabidopsis thaliana* T-DNA insertion line having a disrupted endogenous pectinesterase gene in which said functional pectinesterase protein is not expressed.

In another aspect, the present invention provides a method for producing a plant having improved drought resistance compared to a control plant, comprising the step of impairing expression of functional pectinesterase protein in a plant, plant protoplast or plant cell, wherein said functional pectinesterase protein is encoded by a nucleic acid sequence comprising a nucleic acid sequence having at least 60% identity with the nucleic acid sequence of SEQ ID. No. 1, and optionally regenerating said plant.

The functional pectinesterase protein may be a protein that, when expressed in an *Arabidopsis thaliana* T-DNA insertion line having a disrupted endogenous pectinesterase gene, results in a plant with an impaired drought resistance compared to the drought resistance of said *Arabidopsis thaliana* T-DNA insertion line having a disrupted endogenous pectinesterase gene in which said functional pectinesterase protein is not expressed.

Said step of impairing expression may comprise mutating a nucleic acid sequence encoding said functional pectinesterase protein. Said step of mutating said nucleic acid sequence may involves inserting, a deleting and/or substituting at least one nucleotide.

Said step of impairing expression may comprise gene silencing.

The method may comprise impairing expression of two or more functional pectinesterase proteins. It may further comprise the step of producing a plant or plant product from the plant having improved drought resistance.

In another aspect, the present invention pertain to use of an amino acid sequence having at least 55% identity with the amino acid sequence of SEQ ID. No. 2 or a nucleic acid sequence having at least 60% identity with the nucleic acid sequence of SEQ ID. No. 1 in screening for drought resistance in plants.

Additionally, use of a pectinesterase amino acid sequence of SEQ ID No.2 or a pectinesterase nucleic acid sequence of SEQ ID No. 1 in screening for drought resistance in *Arabidopsis thaliana* plants is taught herein.

The invention is also concerned with use of at least part of a pectinesterase nucleic acid sequence having SEQ ID No.1 or at least part of a pectinesterase amino acid sequence of SEQ ID No.2 as a marker for breeding drought resistant *Arabidopsis thaliana* plants.

The invention further deals with use of a functional pectinesterase protein as defined herein for modulating, preferably increasing, drought resistance of a plant.

Additionally, the invention pertain to the use of a plant, plant cell, or plant product wherein expression of functional pectinesterase protein is impaired, wherein the functional pectinesterase protein is a protein that when expressed in an *Arabidopsis thaliana* T-DNA insertion line having a disrupted endogenous pectinesterase gene results in a plant with an impaired drought resistance compared to the drought resistance of said *Arabidopsis thaliana* T-DNA insertion line having a disrupted endogenous pectinesterase gene in which said functional pectinesterase protein is not expressed for growing under drought stress conditions, wherein said drought stress conditions cause a control plant, plant cell or plant product wherein expression of said functional pectinesterase protein is not impaired to show signs of drought stress such as wilting signs earlier than the plant, plant cell, or plant product wherein expression of functional pectinesterase protein is impaired.

Finally, the invention provides a *Solanum lycopersicum, Gossypium hirsutum, Glycine max, Triticum* spp., *Hordeum vulgare., Avena sativa, Sorghum bicolor, Secale cereale*, or *Brassica napus* plant, plant cell, or plant product wherein expression of functional pectinesterase protein is impaired, wherein the functional pectinesterase protein is a protein that when expressed in an *Arabidopsis thaliana* T-DNA insertion line having a disrupted endogenous pectinesterase gene results in a plant with an impaired drought resistance compared to the drought resistance of said *Arabidopsis thaliana* T-DNA insertion line having a disrupted endogenous pectinesterase gene in which said functional pectinesterase protein is not expressed. In an embodiment, said plant, plant cell, or plant product comprises a disrupted endogenous pectinesterase gene.

DEFINITIONS

Figure 1:
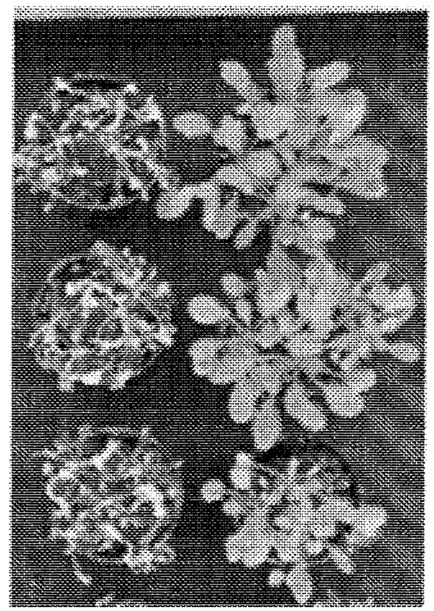
FIG. 1 shows the results of a typical experiment described in Examples 1 and 2.

In the following description and examples, a number of terms are used. In order to provide a clear and consistent understanding of the specification and claims, including the scope to be given to such terms, the following definitions are provided. Unless otherwise defined herein, all technical and scientific terms used have the same meaning as commonly understood by one of ordinary skill in the art to which this invention belongs. The disclosures of all publications, patent applications, patents and other references are incorporated herein in their entirety by reference.

Methods of carrying out the conventional techniques used in methods of the invention will be evident to the skilled worker. The practice of conventional techniques in molecular biology, biochemistry, computational chemistry, cell culture, recombinant DNA, bioinformatics, genomics, sequencing and related fields are well-known to those of skill in the art and are discussed, for example, in the following literature references: Sambrook et al., Molecular Cloning. A Laboratory Manual, 2nd Edition, Cold Spring Harbor Laboratory Press, Cold Spring Harbor, N. Y., 1989; Ausubel et al., Current Protocols in Molecular Biology, John Wiley & Sons, New York, 1987 and periodic updates; and the series Methods in Enzymology, Academic Press, San Diego.

In this document and in its claims, the verb "to comprise" and its conjugations is used in its non-limiting sense to mean that items following the word are included, but items not specifically mentioned are not excluded. It encompasses the verbs "consisting essentially of" as well as "consisting of".

As used herein, the singular forms "a," "an" and "the" include plural referents unless the context clearly dictates otherwise. For example, a method for isolating "a" DNA molecule, as used above, includes isolating a plurality of molecules (e.g. 10's, 100's, 1000's, 10's of thousands, 100's of thousands, millions, or more molecules).

Aligning and alignment: With the term "aligning" and "alignment" is meant the comparison of two or more nucleotide sequences based on the presence of short or long stretches of identical or similar nucleotides. Several methods for alignment of nucleotide sequences are known in the art, as will be further explained below.

"Expression of a gene" refers to the process wherein a DNA region, which is operably linked to appropriate regulatory regions, particularly a promoter, is transcribed into an RNA, which is biologically active, i.e. which is capable of being translated into a biologically active protein or peptide (or active peptide fragment) or which is active itself (e.g. in posttranscriptional gene silencing or RNAi). An active protein in certain embodiments refers to a protein being constitutively active. The coding sequence is preferably in sense-orientation and encodes a desired, biologically active protein or peptide, or an active peptide fragment. "Ectopic expression" refers to expression in a tissue in which the gene is normally not expressed.

"Functional", in relation to pectinesterase proteins (or variants, such as orthologs or mutants, and fragments), refers to the capability to of the gene and/or encoded protein to modify the (quantitative and/or qualitative) drought tolerance, e.g., by modifying the expression level of the gene (e.g. by overexpression or silencing) in a plant. For example, the functionality of a pectinesterase protein obtained from plant species X can be tested by various methods. Preferably, if the protein is functional, silencing or knocking out of the gene encoding the pectinesterase protein in plant species X, using e.g. gene silencing vectors, will lead to an improved drought resistance as can be tested as explained herein in detail. Also, complementation of an *Arabidopsis thaliana* T-DNA insertion line having a disrupted pectinesterase gene with a nucleic acid sequence encoding said functional pectinesterase protein results in a plant in which normal drought resistance is restored, i.e. the complemented plant will have a drought resistance similar to a control plant. The skilled person will be able to test functionality of a pectinesterase protein using routine methods as exemplified herein.

The term "gene" means a DNA sequence comprising a region (transcribed region), which is transcribed into an RNA molecule (e.g. an mRNA) in a cell, operably linked to suitable regulatory regions (e.g. a promoter). A gene may thus comprise several operably linked sequences, such as a promoter, a 5' leader sequence comprising e.g. sequences involved in translation initiation, a (protein) coding region (cDNA or genomic DNA), and a 3' non-translated sequence (also known as 3' untranslated sequence or 3'UTR) comprising e.g. transcription termination sequence sites.

The term "cDNA" means complementary DNA. Complementary DNA is made by reverse transcribing RNA into a complementary DNA sequence. cDNA sequences thus correspond to RNA sequences that are expressed from genes. As mRNA sequences when expressed from the genome can undergo splicing, i.e. introns are spliced out of the mRNA and exons are joined together, before being translated in the cytoplasm into proteins, it is understood that expression of a cDNA means expression of the mRNA that encodes for the cDNA. The cDNA sequence thus may not be identical to the genomic DNA sequence to which it corresponds as cDNA may encode only the complete open reading frame, consisting of the joined exons, for a protein, whereas the genomic DNA encodes exons interspersed by intron sequences, which are flanked by 5' and 3' UTR sequences.

"Identity" is a measure of the identity of nucleotide sequences or amino acid sequences. In general, the sequences are aligned so that the highest order match is obtained. "Identity" per se has an art-recognized meaning and can be calculated using published techniques. See, e.g.: (COMPUTATIONAL MOLECULAR BIOLOGY, Lesk, A. M., ed., Oxford University Press, New York, 1988; BIOCOMPUTING: INFORMATICS AND GENOME PROJECTS, Smith, D. W., ed., Academic Press, New York, 1993; COMPUTER ANALYSIS OF SEQUENCE DATA, PART I, Griffin, A. M., and Griffin, H. G., eds., Humana Press, New Jersey, 1994; SEQUENCE ANALYSIS IN MOLECULAR BIOLOGY, von Heinje, G., Academic Press, 1987; and SEQUENCE ANALYSIS PRIMER; Gribskov, M. and Devereux, J., eds., M Stockton Press, New York, 1991). While a number of methods exist to measure identity between two polynucleotide or polypeptide sequences, the term "identity" is well known to skilled artisans (Carillo, H., and Lipton, D., SIAM J. Applied Math (1988) 48:1073). Methods commonly employed to determine identity or similarity between two sequences include, but are not limited to, those disclosed in GUIDE TO HUGE COMPUTERS, Martin J. Bishop, ed., Academic Press, San Diego, 1994, and Carillo, H., and Lipton, D., SIAM J. Applied Math (1988) 48:1073. Methods to determine identity and similarity are codified in computer programs. Preferred computer program methods to determine identity and similarity between two sequences include, but are not limited to, GCS program package (Devereux, J., et al., Nucleic Acids Research (1984) 12(1):387), BLASTP, BLASTN, FASTA (Atschul, S. F. et al., J. Molec. Biol. (1990) 215:403).

As an illustration, by a polynucleotide having a nucleotide sequence having at least, for example, 95% "identity" to a reference nucleotide sequence encoding a polypeptide of a certain sequence it is intended that the nucleotide sequence of the polynucleotide is identical to the reference sequence except that the polynucleotide sequence may include up to five point mutations per each 100 nucleotides of the reference polypeptide sequence. Hence, the percentage of identity of a nucleotide sequence to a reference nucleotide sequence is to be calculated over the full length of the reference nucleotide sequence. In other words, to obtain a polynucleotide having a nucleotide sequence at least 95% identical to a reference nucleotide sequence, up to 5% of the nucleotides in the reference sequence may be deleted and/or substituted with another nucleotide, and/or a number of nucleotides up to 5% of the total nucleotides in the reference sequence may be inserted into the reference sequence. These mutations of the reference sequence may occur at the 5' or 3' terminal positions of the reference nucleotide sequence, or anywhere between those terminal positions, interspersed either individually among nucleotides in the reference sequence or in one or more contiguous groups within the reference sequence.

Similarly, by a polypeptide having an amino acid sequence having at least, for example, 95% "identity" to a reference amino acid sequence of SEQ ID NO: 2 is intended that the amino acid sequence of the polypeptide is identical to the reference sequence except that the polypeptide sequence may include up to five amino acid alterations per each 100 amino acids of the reference amino acid of SEQ ID NO: 2. Hence, the percentage of identity of an amino acid sequence to a reference amino acid sequence is to be calculated over the full length of the reference amino acid sequence. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino- or carboxy-terminal positions of the reference amino acid sequence or anywhere between those terminal positions, interspersed either individually among residues in the reference sequence or in one or more contiguous groups within the reference sequence.

A nucleic acid according to the present invention may include any polymer or oligomer of pyrimidine and purine bases, preferably cytosine, thymine, and uracil, and adenine and guanine, respectively (See Albert L. Lehninger, *Principles of Biochemistry*, at 793-800 (Worth Pub. 1982), which is herein incorporated by reference in its entirety for all purposes). The present invention contemplates any deoxyribonucleotide, ribonucleotide or peptide nucleic acid component, and any chemical variants thereof, such as methylated, hydroxymethylated or glycosylated forms of these bases, and the like. The polymers or oligomers may be heterogenous or homogenous in composition, and may be isolated from naturally occurring sources or may be artificially or synthetically produced. In addition, the nucleic acids may be DNA or RNA, or a mixture thereof, and may exist permanently or transitionally in single-stranded or double-stranded form, including homoduplex, heteroduplex, and hybrid states.

As used herein, the term "operably linked" refers to a linkage of polynucleotide elements in a functional relationship. A nucleic acid is "operably linked" when it is placed into a functional relationship with another nucleic acid sequence. For instance, a promoter, or rather a transcription regulatory sequence, is operably linked to a coding sequence if it affects the transcription of the coding sequence. Operably linked means that the DNA sequences being linked are typically contiguous and, where necessary to join two or more protein encoding regions, contiguous and in reading frame.

"Plant" refers to either the whole plant or to parts of a plant, such as cells, tissue or organs (e.g. pollen, seeds, gametes, roots, leaves, flowers, flower buds, anthers, fruit, etc.) obtainable from the plant, as well as derivatives of any of these and progeny derived from such a plant by selfing or crossing. "Plant cell(s)" include protoplasts, gametes, suspension cultures, microspores, pollen grains, etc., either in isolation or within a tissue, organ or organism.

As used herein, the term "promoter" refers to a nucleic acid sequence that functions to control the transcription of one or more genes, located upstream with respect to the direction of transcription of the transcription initiation site of the gene, and is structurally identified by the presence of a binding site for DNA-dependent RNA polymerase, transcription initiation sites and any other DNA sequences, including, but not limited to transcription factor binding sites, repressor and activator protein binding sites, and any other sequences of nucleotides known to one of skill in the art to act directly or indirectly to regulate the amount of transcription from the promoter. Optionally the term "promoter" includes herein also the 5' UTR region (5' Untranslated Region) (e.g. the promoter may herein include one or more parts upstream (5') of the translation initiation codon of a gene, as this region may have a role in regulating transcription and/or translation. A "constitutive" promoter is a promoter that is active in most tissues under most physiological and developmental conditions. An "inducible" promoter is a promoter that is physiologically (e.g. by external application of certain compounds) or developmentally regulated. A "tissue specific" promoter is only active in specific types of tissues or cells. A "promoter active in plants or plant cells" refers to the general capability of the promoter to drive transcription within a plant or plant cell. It does not make any implications about the spatio-temporal activity of the promoter.

The terms "protein" or "polypeptide" are used interchangeably and refer to molecules consisting of a chain of amino acids, without reference to a specific mode of action, size, 3 dimensional structure or origin. A "fragment" or "portion" of a protein may thus still be referred to as a "protein". An "isolated protein" is used to refer to a protein which is no longer in its natural environment, for example in vitro or in a recombinant bacterial or plant host cell.

"Transgenic plant" or "transformed plant" refers herein to a plant or plant cell having been transformed, e.g. by the introduction of a non-silent mutation in an endogenous gene or part there of. Such a plant has been genetically modified to introduce for example one or more mutations, insertions and/or deletions in the gene and/or insertions of a gene silencing construct in the genome. A transgenic plant cell may refer to a plant cell in isolation or in tissue culture, or to a plant cell contained in a plant or in a differentiated organ or tissue, and both possibilities are specifically included herein. Hence, a reference to a plant cell in the description or claims is not meant to refer only to isolated cells or protoplasts in culture, but refers to any plant cell, wherever it may be located or in whatever type of plant tissue or organ it may be present.

Targeted nucleotide exchange (TNE) is a process by which a synthetic oligonucleotide, partially complementary to a site in a chromosomal or an episomal gene directs the reversal of a single nucleotide at a specific site. TNE has been described using a wide variety of oligonucleotides and targets. Some of the reported oligonucleotides are RNA/DNA chimeras, contain terminal modifications to impart nuclease resistance.

As used herein, the term "drought stress" or "drought" refers to a sub-optimal environmental condition associated with limited availability of water to a plant. Limited availability of water may occur when, for instance, rain is absent or lower and/or when the plants are watered less frequently than required. Limited water availability to a plant may also occur when for instance water is present in soil, but can not efficiently be extracted by the plant. For instance, when soils strongly bind water or when the water has a high salt content, it may be more difficult for a plant to extract the water from the soil. Hence, many factors can contribute to result in limited availability of water, i.e. drought, to a plant. The effect of subjecting plants to "drought" or "drought stress" may be that plants do not have optimal growth and/or development. Plants subjected to drought may have wilting signs. For example, plants may be subjected to a period of at least 15 days under specific controlled conditions wherein no water is provided, e.g. without rain fall and/or watering of the plants.

The term "improved drought resistance" refers to plants which, when provided with improved drought resistance, when subjected to drought or drought stress do not show effects or show alleviated effects as observed in control plants not provided with improved drought resistance. A normal plant has some level of drought resistance. It can easily be determined whether a plant has improved drought resistant by comparing a control plant with a plant provided with improved drought resistance under controlled conditions chosen such that in the control plants signs of drought can be observed after a certain period, i.e. when the plants are subjected to drought or drought stress. The plants with improved drought resistance will show less and/or reduced signs of having been subjected to drought, such as wilting, as compared to the control plants. The skilled person knows how to select suitable conditions such as for example the controlled conditions in the examples. When a plant has "improved drought resistance", it is capable of sustaining normal growth and/or normal development when being subjected to drought or drought stress would otherwise would have resulted in reduced growth and/or reduced development of normal plants. Hence, "improved drought resistance" is a relative term determined by comparing plants, whereby the plant most capable of sustaining (normal) growth under drought stress is a plant with "improved drought resistance". The skilled person is well aware how to select appropriate conditions to determine drought resistance of a plant and how to measure signs of droughts, such as described in for example manuals provided by the IRRI, Breeding rice for drought prone environments, Fischer et al., 2003, and by the CIMMYT, Breeding for drought and nitrogen stress tolerance in maize: from theory to practice, Banzinger et al, 2000. Examples of methods for determining improved drought resistance in plants are provided in Snow and Tingey, 1985, Plant Physiol, 77, 602-7 and Harb et al., Analysis of drought stress in *Arabidopsis*, AOP 2010, Plant Physiology Review, and as described in the example section below.

DETAILED DESCRIPTION OF THE INVENTION

The present invention relates to a method for modulating, e.g., improving, drought resistance of a plant by modifying, e.g., impairing, the expression of a functional pectinesterase protein in said plant, e.g., using genetic modification or targeted nucleotide exchange. The modulation such as improvement is relative to a control plant in which the expression of a functional pectinesterase protein is not modified, e.g., impaired. In other words, a modified plant according to the invention is, in comparison to the non-modified plant, better able to grow and survive under conditions of reduced water availability, (temporary) water-deprivation or conditions of drought. It is understood that according to the invention modifying, e.g., impairing, expression of a functional pectinesterase protein may involve genetic modification, e.g., of the pectinesterase gene expression, or targeted nucleotide exchange.

In an embodiment, the present invention provides a method for improving drought resistance of a plant by impairing the expression of a functional pectinesterase protein in said plant, e.g., using genetic modification or targeted nucleotide exchange.

Genetic modification includes introducing mutations, insertions, deletions in the nucleic acid sequence and/or insertion of gene silencing constructs into a genome of a plant or plant cell that target the nucleic acid sequence. Genetically modifying a nucleic acid sequence, e.g., gene, which encodes the mRNA may not only relate to modifying exon sequences corresponding to the mRNA sequence, but may also involve mutating intronic sequences of genomic DNA and/or (other) gene regulatory sequences of that nucleic acid sequence, e.g., gene.

In an embodiment, the functional pectinesterase protein may be a protein that, when expressed in an *Arabidopsis thaliana* T-DNA insertion line having a disrupted endogenous pectinesterase gene, such as an At5g19730 knockout line, e.g., SALK_1365560 (http://www.arabidopsis.org/servlets/SeedSearcher?action=detail&stock_number=SALK_136556C) recited herein, results in a plant with an impaired drought resistance compared to the drought resistance of said *Arabidopsis thaliana* T-DNA insertion line having a disrupted endogenous pectinesterase gene, e.g., an At5g19730 knockout line, e.g., SALK_1365560, in which said functional pectinesterase protein is not expressed.

The term "disrupted endogenous pectinesterase gene" as used herein refers to a pectinesterase gene naturally present in the genome of a plant which is disrupted, e.g., interrupted, e.g., by means of a T-DNA insertion into said pectinesterase gene. Disruption of said endogenous pectinesterase gene may result in the absence of expression of said endogenous pectinesterase gene.

The term "control plant" as used herein refers to a plant of the same species, preferably of the same variety, preferably of the same genetic background. However, the modification introduced into said control plant is preferably not present or introduced into said control plant.

The current invention also relates to the modulation of drought resistance of a plant by modifying the expression of a functional pectinesterase protein in said plant. The modulation is relative to a control plant (preferably a plant of the same genetic background) in which such modification has not been introduced or is not present.

"Impairing expression of a functional pectinesterase protein" as used herein may mean that the gene expression of the pectinesterase gene is impaired, and/or that expression of the pectinesterase gene is normal but translation of the resulting mRNA is inhibited or prevented (for example, by RNA interference), and/or that the amino acid sequence of pectinesterase protein has been altered such that its pectinesterase specific activity is reduced compared to the pectinesterase specific activity of the protein comprising the amino acid sequence as depicted in SEQ ID NO:2, preferably under physiological conditions, particularly identical physiological conditions. Alternatively, a pectinesterase protein may become less functional or non-functional by scavenging the protein using, for example, an antibody, or a pectinesterase inhibitor. For example, an antibody specifically binding to said pectinesterase protein may be simultaneously expressed, thereby reducing specific activity of the pectinesterase protein. The phrase "impairing expression of a functional pectinesterase protein" as used herein further encompasses scavenging of functional pectinesterase protein by increased expression of pectinesterase inhibitors, e.g., proteins that stop, prevent or reduce the activity of a pectinesterase protein. A non-limiting example of such pectinesterase inhibitor is gene At1 g48020. Alternatively, a chemical pectinesterase inhibitor may be employed, such as ions, or metals, or co-factors of pectinesterase may be scavenged thus reducing their availability for pectinesterase activity. Thus, the phrase includes the situation in which a pectinesterase protein is expressed at a normal level but in which said pectinesterase protein has no or a reduced activity as compared to the pectinesterase protein comprising an amino acid sequence as set forth in SEQ ID NO:2, either by mutation of the amino acid sequence of by scavenging of the (optionally functional) pectinesterase protein.

Pectinesterase catalyzes the de-esterification of pectin into pectate and methanol. Pectin is one of the main components of the plant cell wall. The specific activity of a pectinesterase protein may be considered "reduced" if the specific activity with respect to de-esterification of pectin of such pectinesterase is statistically significantly less than the specific activity of the pectinesterase as depicted in SEQ ID NO:2. The specific activity of a pectinesterase protein may, for example, be reduced by at least 5%, 10%, 15%, 20%, 25%, 30%, 35%, 40%, 45%, 50%, or more. Reduced expression of the endogenous pectinesterase gene of a plant may, for example, be accomplished by altering the promoter sequence, for example, using targeted nucleotide exchange.

The skilled person is capable of determining the specific activity of pectinesterase. For example, PE enzyme activity may be determined by titration as described by Tucker et al. (Tucker G A, et al. (1982). J Sci Food Agric 33 396-400).

It is believed by the current inventors that impairing expression of functional pectinesterase protein (e.g. by reducing, repressing or deleting expression and/or activity) leads to the absence or a reduced level of functional pectinesterase protein, either as a consequence of low expression, e.g. by RNA interference or as the consequence of decreased activity/functionality of the pectinesterase protein, or one or more of the above, and that said absence or reduced level of functional pectinesterase protein leads to decreased need for water or improved resistance to drought of said plant.

The pectinesterase protein of *Arabidopsis thaliana* is comprised of 383 amino acids (the amino acid sequence is depicted in SEQ ID NO:2). The cDNA derived from the pectinesterase gene of *Arabidopsis thaliana* comprises 1149 nucleotides and the nucleic acid sequence thereof is depicted in SEQ ID NO:1.

The term "pectinesterase protein" as used herein refers to the protein comprising the amino acid sequence as depicted in SEQ ID NO:2, as well as fragments and variants thereof. Variants of a pectinesterase protein include, for example, proteins having at least 40%, 50%, 60%, 70%, 75%, 80%, 85%, 90%, 95%, 96%, 97%, 98%, 99%, or more, such as 100%, amino acid sequence identity, preferably over the entire length, to the amino acid sequence of SEQ ID NO:2. Amino acid sequence identity may be determined by pairwise alignment using the Needleman and Wunsch algorithm and GAP default parameters as defined above.

In another aspect there is provided for a method for increasing drought resistance of a plant, the method comprising the step of impairing the expression in said plant of a gene encoding a pectinesterase protein.

"Impaired expression of a gene" according to the present invention denotes the absence or reduced presence of a functional pectinesterase protein. A skilled person is well aware of the many mechanism available to him in the art to impair the expression of a gene at, for example, the transcriptional level or the translational level.

Impairment at the transcriptional level can be the result of the introduction of one or more mutations in transcription regulation sequences, including promoters, enhancers, initiation, termination or intron splicing sequences. These sequences are generally located 5' of, 3' of, or within the coding sequence of the pectinesterase gene of the invention. Independently, or simultaneously, impairment of expression can also be provided by deletion, substitution, rearrangement or insertion of nucleotides in the coding region of the genes.

For example, in the coding region, nucleotides may be substituted, inserted or deleted leading to the introduction of one, two or more premature stop-codons. Also, insertion, deletion, rearrangement or substitution can lead to modifications in the amino acid sequence encoded, and thereby providing for impaired expression of functional pectinesterase protein. Even more, large parts of the genes may be removed, for example, at least 10%, 20%, 30%, 40%, 50%, 60%, 70%, 80%, 90% or even 100% of the (coding region) of the gene is removed from the DNA present in the plant, thereby impairing the expression of functional pectinesterase protein.

Alternatively, one, two, three of more nucleotides may be introduced in the gene or genes coding for a pectinesterase protein, either leading to, for example, a frame-shift, or leading to the introduction of a sequence encoding additional amino acids, or the introduction of a sequence not encoding amino acids, or the introduction of large inserts, thereby impairing the provision/expression of functional pectinesterase protein.

In other words, deletion, substitution or insertion of nucleotide(s) in a nucleotide sequence encoding a pectinesterase protein, as described above, may lead to, for example, a frame shift, an introduction of a stop codon, or the introduction of a non-sense codon. In particular the introduction of a stop codon and the introduction of a frame shift mutation are generally accepted as efficient ways to produce a knockout plant, that is, a plant with reduced, repressed or deleted expression and/or activity of a specific protein.

A frame shift mutation (also called a framing error or a reading frame shift) is a genetic mutation caused by indels (insertions or deletions) of a number of nucleotides that is not evenly divisible by three in a nucleotide sequence. Due to the triplet nature of gene expression by codons, the insertion or deletion can change the reading frame (the grouping of the codons), resulting in a completely different translation from the original. The earlier in the sequence the deletion or insertion occurs, the more altered the protein produced is. A frame shift mutation will in general cause the reading of the codons after the mutation to code for different amino acids, but there may be exceptions resulting from the redundancy in the genetic code. Furthermore, the stop codon ("UAA", "UGA" or "UAG") in the original sequence will not be read, and an alternative stop codon may result at an earlier or later stop site. The protein created may be abnormally short or abnormally long.

The introduction of a stop codon in a nucleotide sequence encoding a pectinesterase protein as defined herein may result in a premature stop of transcription, which generally results in a truncated, incomplete, and non-functional pectinesterase protein. Preferably, the stop codon is introduced early in the transcription direction. The earlier in the nucleotide sequence the stop codon is introduced, the shorter and the more altered the protein produced is. The introduction of a nonsense codon in a nucleotide sequence encoding a pectinesterase protein may result in transcript mRNA wherein e.g. one codon no longer codes for the amino acid as naturally occurring in pectinesterase, for example a codon that normally codes for an amino acid which is essential for a pectinesterase protein to be functional. Hence, such pectinesterase protein may not be functional.

In other words, the impairment may comprise mutating one or more nucleotides in the genes or nucleic acid sequences disclosed herein resulting either in the presence of less or even in the total absence of protein expression product (i.e. the absence of protein that would be obtained when the genes according to the invention were not modified as described above), or in the presence of non-functional protein.

Therefore, in an embodiment of the method disclosed herein, the impairment is the consequence of one or more mutations in said pectinesterase gene resulting in the presence of less protein expression product or absence of a protein expression product as compared to a control plant.

The term inhibition/presence of less protein expression product as used herein relates to a reduction in protein expression of at least 10%, 20%, 30%, 40%, 50%, 60%, 70%, 80%, 90% or even 99% in comparison to a control plant, in which the expression is not impaired. The term "absence of protein expression" refers to the virtual absence of any expression product, for example less than 5%, 4%, 3%, 2% or even less than 1% in comparison to the control.

As will be understood by a skilled person, a mutation may also be introduced in a nucleotide sequence encoding pectinesterase as defined herein by the application of mutagenic compounds, such as ethyl methanesulfonate (EMS) or other compounds capable of (randomly) introducing mutations in nucleotide sequences. Said mutagenic compounds or said other compound may be used as a means for creating plants harboring a mutation in a nucleotide sequence encoding a pectinesterase protein.

Alternatively, the introduction of a mutation in a nucleotide sequence encoding a pectinesterase protein according to the invention may be effected by the introduction of transfer-DNA (T-DNA) in the nucleotide sequence encoding such protein, for instance T-DNA of the tumor-inducing (Ti)

plasmid of some species of bacteria such as *Agrobacterium tumefaciens*. A T-DNA element may be introduced in said nucleotide sequence, leading to either a non-functional protein or to the absence of expression of the protein, consequently decreasing the need for water of a plant obtained by the method according to the invention (see for example Krysan et al. 1999 The Plant Cell, Vol 11. 2283-2290). Likewise advantage can be taken from the use of transposable element insertion (See for Example Kunze et al (1997) Advances in Botanical Research 27 341-370 or Chandlee (1990) Physiologia Planta 79(1) 105-115).

In an embodiment, introducing a mutation in a nucleotide sequence encoding a protein according to the invention may be performed by TNE, for instance as described in WO2007073170. By applying TNE, specific nucleotides can be altered in a nucleotide sequence encoding pectinesterase, whereby, for instance, a stop codon may be introduced which may, for instance, result in a nucleotide sequence encoding a truncated protein with decreased or disappeared pectinesterase activity.

In another embodiment a method is provided as disclosed above wherein the impairment of expression of functional pectinesterase protein is caused by expression of non-functional protein or a protein with reduced functionality. As explained above, a skilled person has no problem in determining functionality of the genes according to the invention. For example, he may perform complementation studies, by introducing the control gene, without any modifications, into a plant in which the expression of a protein according to the invention has been impaired and study drought resistance.

Alternatively, he may perform experiments analogous to the experiments described in the examples below, and determine drought resistance in a plant in which one or more mutations were introduced in the genes according to the invention, by comparison to a suitable control/wild-type plant.

Impairment can also be provided at the translational level, e.g. by introducing a premature stop-codon or by posttranslational modifications influencing, for example, protein folding.

Independent of the mechanism, impairment according to the present invention is indicated by the absence or reduced presence of functional pectinesterase protein, including the presence of normal levels of dysfunctional pectinesterase protein.

As explained above the term inhibition of expression or reduced presence as used herein relates to a reduction in protein expression of at least 10%, 20%, 30%, 40%, 50%, 60%, 70%, 80%, 90% or even 99% in comparison to a control plant, in which the expression is not impaired. The term "absence of protein expression" refers to the virtual absence of any expression product, for example less than 5%, 4%, 3%, 2% or even less than 1% in comparison to the control.

According to another embodiment, said impairment is caused by gene silencing, for example RNA interference or RNA silencing.

With the help of molecular biology methods readily available to the skilled person, impairment of the genes can also be accomplished by gene silencing, for example using RNA interference techniques, dsRNA or other expression silencing techniques (see for example, Kusaba et. al (2004) Current Opinion in Biotechnology 15:139-143, or Preuss and Pikaard (2003) in RNA Interference (RNAi)~Nuts & Bolts of siRNA Technology (pp. 23-36), ©2003 by DNA Press, LLC Edited by: David Engelke, Ph.D.) or, as already discussed above, knocking out.

In another preferred embodiment, and as already discussed above, a method according to the invention is provided wherein the impairment is caused by insertion, deletion and/or substitution of at least one nucleotide. For example, 1, 2, 3 . . . 10, 40, 50, 100, 200, 300, 1000, or even more nucleotides may be inserted, deleted or substituted in the genes according to the invention. Also anticipated are combinations of insertion, deletion and/or substitution, either in the coding or in the non-coding regions of the gene.

In another embodiment of the method disclosed herein the method comprises the step of impairing the expression in said plant of more than 1, for example 2, 3, 4, 5, or all genes encoding a pectinesterase protein.

In this embodiment, the expression of more than one gene as described above, present in a particular plant is impaired. For example the expression of one, two, three, four, or all of the genes encoding a pectinesterase protein, as present in a plant, is impaired. By impairing the expression of more genes as described above at the same time (when present in a plant) even more improved drought resistance can be achieved.

In another embodiment, the plant provided by the method according to the invention can be used for the production of further plants and or plant products derived there from. The term "plant products" refers to those material that can be obtained from the plants grown, and include fruits, leaves, plant organs, plant fats, plant oils, plant starch, plant protein fractions, either crushed, milled or still intact, mixed with other materials, dried, frozen, and so on. In general such plant products can, for example, be recognized by the presence of a gene as disclosed herein so modified that the expression of a functional protein is impaired, as detailed above.

Preferably, expression and/or activity of the pectinesterase protein according to the invention is impaired (e.g. reduced, repressed or deleted) in a plant belonging to the Brassicaceae family including *Brassica napus* (rape seed), Solanaceae-family, including tomato, or Curcurbitaceae family, including melon and cucumber, or the Poaceae family including *Oryza*, including rice, or *Zea mays*, including maize (corn), or the Fabaceae including legume, pea, or bean. Preferably the method according to the invention is applied in tomato, rice, maize, melon, or cucumber, thereby providing a plant with decreased need for water or improved resistance to drought in comparison to a corresponding control plant.

Also provided is a plant cell, plant or plant product derived thereof obtainable by the method according to the invention, and wherein said plant cell, plant or plant product shows reduced expression of functional pectinesterase protein, compared to a control plant not subjected to the method according to the invention.

Also provided is a plant cell, plant or plant product derived thereof, characterized in that in said plant cell, plant or plant product derived thereof the expression of at least one, preferably all genes encoding a pectinesterase protein, such as those wherein the cDNA sequence corresponding to the mRNA sequence transcribed from said at least one gene comprises the sequence shown in SEQ ID NO:1, and cDNA sequences with more than 40%, 50%, 60%, 70%, 80%, 90%, 95% identity with the nucleotide sequence of SEQ ID NO:1 and/or wherein the amino acid sequence encoded by said at least one gene comprises the sequence shown in SEQ ID NO:2 or a variant thereof, is impaired. Preferably the plant is not the *Arabidopsis thaliana* mutant as described in the examples below, or a *Brachypodium* T-DNA insertion mutant.

In another aspect, the invention is directed to use of a gene wherein the cDNA sequence corresponding to the mRNA sequence transcribed from said gene comprises the sequence shown in SEQ ID NO:1, and cDNA sequences with more than 40%, 50%, 60%, 70%, 80%, 90%, 95% identity therewith and/or wherein the amino acid sequence encoded by said gene comprises the sequence shown in SEQ ID NO:2, and amino acid sequences with more than 40%, 50%, 60%, 70%, 80%, 90%, 95% identity therewith, for providing increased drought resistance to a plant.

In this embodiment, the gene described can be used as a target for improving drought resistance in a plant, in accordance with the disclosure herein, or the gene can be used to identify new proteins involved in drought sensitivity and resistance.

In another embodiment a use is provided of a pectinesterase sequence having SEQ ID No.1 or 2 of the *Arabidopsis thaliana* species in the screening for drought resistance in *Arabidopsis thaliana* plants. In addition, a use is provided wherein the pectinesterase sequence is an analogous sequence to SEQ ID No.1 or 2 of an other plant species and wherein the screening is in plants of the other plant species. Furthermore, a method is provided for screening plants or plant cells with improved drought resistance comprising the steps of:

- providing a heterogenic population of plant cells or plants of the *Arabidopsis thaliana* species;
- providing a pectinesterase sequence having SEQ ID No.1 or 2;
- determining the sequence of at least part of the pectinesterase gene of the plants cells or plants;
- comparing the determined pectinesterase sequences from the plant cells or plants with the provided pectinesterase sequence;
- identifying plant cells or plants wherein the pectinesterase sequence comprises a mutation. Alternatively, in the method, the plant cells or plants that are provided are of an other species, and wherein the pectinesterase gene sequence that is provided is an analogous sequence of the other species.

Hence, by using the pectinesterase sequence SEQ ID No.1 or SEQ ID No.2 of the species *Arabidopsis thaliana*, or an analogous sequence thereof from an other species, mutated pectinesterase sequences can be identified in the plant species that may provide improved drought resistance. An analogous sequence, in another species, of the pectinesterase sequence SEQ ID No.1 or SEQ ID No.2 of the species *Arabidopsis thaliana* is defined as a sequence having at least 40%, 50%, 60%, 70%, 75%, 80%, 85%, 90%, 95%, or at least 99%, sequence identity therewith. The analogous pectinesterase protein may have substantially the same function as SEQ ID No.2. Analogous sequences are depicted as SEQ ID NOs: 3-10 in the sequence listing and are derived from *Brassica rapa, Solanum lycopersicum* and *Oryza sativa*, respectively. Their sequence identities as compared to SEQ ID NO:2 are set forth in Table 2 below.

In the method, a heterogenic population of plant cells or plants of the species is provided. The heterogenic population may for example be provided by subjecting plant cells to a mutagen that introduces random mutations thereby providing a heterogenic population of plant cell. Hence, the heterogenic population may be derived from a single plant variety, which is subjected to random mutagenesis in order to obtain a variety of mutations in the offspring thereby providing a heterogenic population. Many mutagens are known in the art, e.g. ionic radiation, UV-radiation, and mutagenic chemicals such as azides, ethidium bromide or ethyl methanesulfonate (EMS). Hence the skilled person knows how to provide for a heterogenic population of plants or plant cells. Also, the skilled person may also provide a variety of plants as a heterogenic population, i.e. not a single variety from a species. A variety of plants show genetic variety, they are not genetically identical, but because the plants are from the same species they are substantially identical. In any case, a heterogenic population of plant cells or plants may have at least 95%, 96%, 97%, 98%, 98%, 99%, 99.5% or at least 99.9% sequence identity.

By determining at least part of the sequence of the pectinesterase gene sequence with the sequence of the plants or plant cells from the heterogenic population, and subsequently comparing these sequences with the provided pectinesterase gene sequence (the reference), plant cells or plants can be identified that comprise a mutation in the pectinesterase gene sequence. It is understood that such a comparison can be done by alignment of the sequences and that a mutation is a difference in respect of at least one nucleic acid or amino acid position in the analogous (reference) pectinesterase sequence of the plant species. In this way, plants or plant cells are identified that have mutations in the pectinesterase gene (e.g. insertions, deletions, substitutions) that may provide improved drought resistance.

Preferably, plants are selected that have mutations that would result in an impairment of expression of a functional pectinesterase protein, such as already outlined above. Mutations that would impair expression of a functional pectinesterase protein may be mutations that would disrupt the open reading frame (introduce a frame shift or a stop codon) or disrupt or otherwise alter the function of the encoded protein by altering nucleotides in codons encoding amino acids that are essential for the proper functioning of the protein, thereby leading to modified (e.g. increased) resistance to drought in comparison to the non-altered protein. The method may also be used for example in the screening and selection of plants that have been subjected to genetic modification which targets the pectinesterase gene sequence as outlined above. Also, the pectinesterase sequence may also be used in a screening assay, in which a (heterogenic) population of plants are subjected to drought.

In another embodiment, the use is provided of at least part of a pectinesterase sequence having SEQ ID No.1 or SEQ ID No.2 of the *Arabidopsis thaliana* species as a marker for breeding drought resistant *Arabidopsis thaliana* plants. Also, the pectinesterase sequence may be of an analogous sequence of another species wherein the marker is for breeding drought resistant plants of the other plant species.

The invention further pertains to use of a plant, plant cell, or plant product wherein expression of functional pectinesterase protein is impaired, wherein the functional pectinesterase protein is a protein that when expressed in an *Arabidopsis thaliana* T-DNA insertion line having a disrupted endogenous pectinesterase gene results in a plant with an impaired drought resistance compared to the drought resistance of said *Arabidopsis thaliana* T-DNA insertion line having a disrupted endogenous pectinesterase gene in which said functional pectinesterase protein is not expressed for growing under drought stress conditions, wherein said drought stress conditions cause a control plant, plant cell, or plant product wherein expression of said functional pectinesterase protein is not impaired to show signs of drought stress such as wilting signs earlier than the plant, plant cell, or plant product wherein expression of functional pectinesterase protein is impaired.

In an aspect, the present invention pertains to a plant, plant cell or plant product obtainable or obtained by the method taught herein. Additionally, the invention provides a seed derived from such plant.

The invention also relates to a plant, plant cell, or plant product wherein expression of functional pectinesterase protein is impaired, wherein the functional pectinesterase protein is a protein that when expressed in an *Arabidopsis thaliana* T-DNA insertion line having a disrupted endogenous pectinesterase gene in which said functional pectinesterase protein is not expressed. Said plant, plant cell or plant product may, for example, comprise a disrupted endogenous pectinesterase gene.

The plant, plant cell or plant product may be any plant or plant cell, or may be derived from any plant, such as monocotyledonous plants or dicotyledonous plants, but most preferably the plant belongs to the family Solanaceae. For example, the plant may belong to the genus *Solanum* (including *lycopersicum*), *Nicotiana, Capsicum, Petunia* and other genera. The following host species may suitably be used: Tobacco (*Nicotiana* species, e.g. *N. benthamiana, N. plumbaginifolia, N. tabacum*, etc.), vegetable species, such as tomato (*Solanum lycopersicum*) such as e.g. cherry tomato, var. *cerasiforme* or currant tomato, var. *pimpinellifolium*) or tree tomato (*S. betaceum*, syn. *Cyphomandra betaceae*), potato (*Solanum tuberosum*), eggplant (*Solanum melongena*), pepino (*Solanum muricatum*), cocona (*Solanum sessiliflorum*) and naranjilla (*Solanum quitoense*), peppers (*Capsicum annuum, Capsicum frutescens, Capsicum baccatum*), ornamental species (e.g. *Petunia hybrida, Petunia axillaries, P. integrifolia*).

Alternatively, the plant may belong to any other family, such as to the Cucurbitaceae or Gramineae. Suitable host plants include for example maize/corn (*Zea* species), wheat (*Triticum* species), barley (e.g. *Hordeum vulgare*), oat (e.g. *Avena sativa*), sorghum (*Sorghum bicolor*), rye (*Secale cereale*), soybean (*Glycine* spp, e.g. *G. max*), cotton (*Gossypium* species, e.g. *G. hirsutum, G. barbadense*), *Brassica* spp. (e.g. *B. napus, B. juncea, B. oleracea, B. rapa*, etc), sunflower (*Helianthus annus*), safflower, yam, cassava, alfalfa (*Medicago sativa*), rice (*Oryza* species, e.g. *O. sativa* indica cultivar-group or *japonica* cultivar-group), forage grasses, pearl millet (*Pennisetum* spp. e.g. *P. glaucum*), tree species (*Pinus*, poplar, fir, plantain, etc), tea, *coffea*, oil palm, coconut, vegetable species, such as pea, zucchini, beans (e.g. *Phaseolus* species), cucumber, artichoke, asparagus, broccoli, garlic, leek, lettuce, onion, radish, turnip, Brussels sprouts, carrot, cauliflower, chicory, celery, spinach, endive, fennel, beet, fleshy fruit bearing plants (grapes, peaches, plums, strawberry, mango, apple, plum, cherry, apricot, banana, blackberry, blueberry, citrus, kiwi, figs, lemon, lime, nectarines, raspberry, watermelon, orange, grapefruit, etc.), ornamental species (e.g. Rose, *Petunia, Chrysanthemum*, Lily, *Gerbera* species), herbs (mint, parsley, basil, thyme, etc.), woody trees (e.g. species of *Populus, Salix, Quercus, Eucalyptus*), fibre species e.g. flax (*Linum usitatissimum*) and hemp (*Cannabis sativa*), or model organisms, such as *Arabidopsis thaliana.*

Preferred hosts are "crop plants", i.e. plant species which is cultivated and bred by humans. A crop plant may be cultivated for food purposes (e.g. field crops), or for ornamental purposes (e.g. production of flowers for cutting, grasses for lawns, etc.). A crop plant as defined herein also includes plants from which non-food products are harvested, such as oil for fuel, plastic polymers, pharmaceutical products, cork and the like.

Preferably, the plant, plant cell or plant product of the invention is not an *Arabidopsis thaliana* or *Brachypodium* plant, plant cell or plant product.

The plant, plant cell or plant product of the invention may, for example, be a *Solanum lycopersicum* or *Brassica rapa* plant, plant cell or plant product.

For example, the present invention relates to a *Solanum lycopersicum, Gossypium hirsutum, Glycine max, Triticum* spp., *Hordeum vulgare., Avena sativa, Sorghum bicolor, Secale cereale*, or *Brassica napus* plant, plant cell, or plant product wherein expression of functional pectinesterase protein is impaired, wherein the functional pectinesterase protein is a protein that when expressed in an *Arabidopsis thaliana* T-DNA insertion line having a disrupted endogenous pectinesterase gene results in a plant with an impaired drought resistance compared to the drought resistance of said *Arabidopsis thaliana* T-DNA insertion line having a disrupted endogenous pectinesterase gene in which said functional pectinesterase protein is not expressed. Said *Solanum lycopersicum, Gossypium hirsutum, Glycine max, Triticum* spp., *Hordeum vulgare., Avena sativa, Sorghum bicolor, Secale cereale*, or *Brassica napus* plant, plant cell, or plant product may comprise a disrupted endogenous pectinesterase gene.

All references recited herein are herein incorporated by reference in their entirety.

EXAMPLES

Example 1

Drought Test

*Arabidopsis thaliana* (At) seeds transformed with *Agrobacterium tumefaciens* vector pROK2, leading to the absence of functional pectinesterase protein (NASC ID: N664100, AGI code At5g19730 and SALK_1365560; hereafter referred to as mutant seeds or mutant plants) were obtained from the Nottingham *Arabidopsis* Stock Centre (NASC; School of Biosciences, University of Nottingham, Sutton Bonington Campus, Loughborough, LE12 5RD United Kingdom). As control At Col-0 (Columbia, N60000); hereafter referred to as control seed or plant) were used.

Growth Medium:

A soil mixture comprising one part of sand and vermiculite and two parts of compost was used (sand:vermiculite:compost=1:1:2). This mixture increases the water percolation hence facilitates uniform water uptake by each pot and better water drainage. Before sowing, the seeds were kept at 4° C. for 3 days under dark and humid conditions for stratification.

Both mutant and control seeds were sown in a rectangular tray containing 8×5=40 pots of ~4 cm diameter with density of 5 plants per pot. Nutrient solution (EC=1.5) was supplied to all the plants from the bottom of the pots in the tray 10 days after germination (DAG), and at 15 DAG the plants were subjected to drought (for 15, 16, 17 or 18 days) by transferring the pots to dry trays. Subsequently, plants were rehydrated and observed for recovery after 1 week.

Three pot replicates of each genotype were included in the pre-drought screening. Total time needed for a complete test was approx. 36-39 days.

Drought Assay Examination:

Once the plants reached the 2 true leaves stage they were thinned to maintain exactly 5 plants per pot. At 10 DAG, plants received nutrition (EC=1.5) and at 15 DAG each pot was moved to a dry tray. From this day onwards the plants did not receive any water. Every day the plants, especially the control (or wild type) (Col-0) were observed for wilting signs. On the 15$^{th}$ day of drought (DOD), Col-0 wilted completely and did not recover upon rehydration. We determined this day as its permanent wilting point (PWP). From this day onwards one replicate from the mutant was rehydrated and observed for recovery signs and pictures were taken. The mutant showed survival for at least 2 days more under drought compared to the control and was subjected for further rigorous screening.

Example 2

Drought Test

Growth Medium:

The same mutant and control plants as in Example 1 were grown in similar tray set-up as described above in the pre-screening test. Plants were stressed by withholding water from 15 DAG until the control reached its PWP. During this period every alternate day pots were shuffled within the trays to reduce the position effects and allow uniform evaporation. On day 15 DOD, control plants reached PWP and did not recover upon rehydration. One pot replicate from the mutant was rehydrated everyday from 15 DOD onwards and checked for drought stress recovery. Pictures were taken and recovery was scored. The mutant showed recovery from drought stress for at least 3 days more after the control reached its PWP.

FIG. 1 shows a photograph comparing mutant and control, demonstrating the superior effect of the mutant with respect to resistance to drought stress compared to the control.

Example 3

Drought Test

Materials and Methods

Plant Material. A TDNA insertion line with a disrupted AT5G19730 (pectinesterase) gene (SALK_136556C) was obtained from the Nottingham *Arabidopsis* Stock Centre (NASC). Complementation lines were produced by stable transformation of *Arabidopsis thaliana* plants using floral dip transformation (Bent et al., 2006. Methods Mol. Biol. Vol. 343:87-103). Homologs of the *Arabidopsis thaliana* (AT5G19730) pectinesterase gene were identified from several crop species, including *Brassica rapa* (cabbage), *Solanum lycopersicum* (tomato) and *Oryza sativa* (rice) and the model species *Arabidopsis thaliana*.

TABLE 2

Percentage of nucleic acid sequence identity between the *Arabidopsis thaliana* pectinesterase cDNA sequence (SEQ ID NO: 1) and cDNA sequences of homologues in *Brassica rapa* (Br81413; SEQ ID NO: 3), *Solanum lycopersicum* (Slg24530; SEQ ID NO: 5), and *Oryza sativa* (Os01g53990_1 and Os01g53990_2; SEQ ID NO: 7 and 9, respectively) (first column); and percentage of amino acid sequence identity between the *Arabidopsis thaliana* pectinesterase protein sequence (SEQ ID NO: 2) and protein sequences of homologues in *Brassica rapa* (Br81413; SEQ ID NO: 4), *Solanum lycopersicum* (Slg24530; SEQ ID NO: 6), and *Oryza sativa* (Os01g53990_1 and Os01g53990_2; SEQ ID NO: 8 and 10, respectively)(second column).

| Annotation | *Arabidopsis thaliana* | *Brassica rapa* | *Solanum lycopersicum* | *Oryza sativa* |
|---|---|---|---|---|
| Pectinesterase | AT5G19730 (SEQ ID NO: 1 & 2) | Br81413.g42 (SEQ ID NO: 3 & 4) | Slg24530 (SEQ ID NO: 5 & 6) | Os01g53990_1 (SEQ ID NO: 7 & 8) Os01g53990_2 (SEQ ID NO: 9 & 10) |

| | % identity in cDNA sequence | % identity in amino acid sequence |
|---|---|---|
| Br81413 | 89 | 91 |
| Slg24530 | 65 | 57 |
| Os01g53990_1 | 65 | 63 |
| Os01g53990_2 | 64 | 61 |

Drought Assay. Wild-type, TDNA knock-out and complementation lines were sown in a replicated blocked design in 50-cell seedlings trays containing a 2:1:1 mix of Metro-Mix 852 soilless medium, fine sand and vermiculite. Planted trays were placed at 4° C. for three days to break dormancy and then transferred to a growth chamber (16 h 22/20° C., 50% rH) for germination and establishment. Complementation lines were sprayed with a glufosinate formulation (20 mg glufosinate, 20 μL Silwet surfactant, 200 mL water) once they had fully expanded cotyledons to assure that only transformed lines were selected. Following this treatment, seedlings in each cell were thinned to a single plant. Once plants reached the 4-6 true leaf stage they were acclimated to greater vapour pressure deficit conditions to promote even drought stress (28/26° C., 25% rH) and unusually small plants were identified for removal prior to drought treatment. Planting trays were soaked with water and then allowed to drain, leaving all cells at pot capacity. Entire trays were watered once half of the wild-type plants in any given tray appeared to be at their permanent wilting point (1.5-2 weeks of drought treatment). Plants were allowed to recover over a few days and survival was recorded, with pre-identified abnormally small plants omitted from further analyses.

Statistical Analysis. Statistical significance of differing probabilities of survival over this drought treatment was assessed by applying the test of equal or given proportions in the statistical software program, R (http://www.r-project.org/). The function prop.test was used to test the null hypothesis that the proportions of surviving plants between mutant and wild-type (one-tailed), or alternatively, between insertion mutant lines containing or not containing complementing transgenes (two-tailed), were equal.

Results

Figure 2:
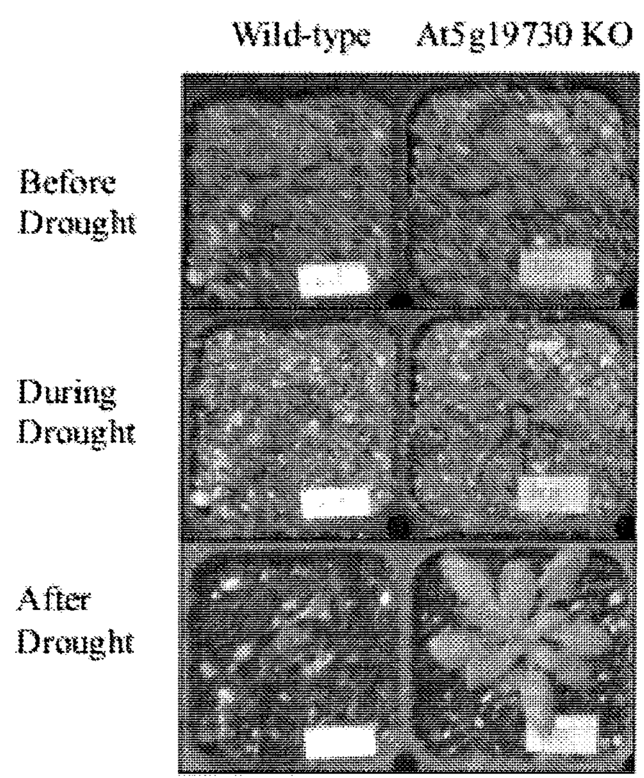
FIG. 2 shows the drought resistant phenotype of the pectinesterase knockout (*Arabidopsis* At5g19730 insertion mutant) as compared to the drought sensitive phenotype of a control (wild-type) plant.
Figure 3:
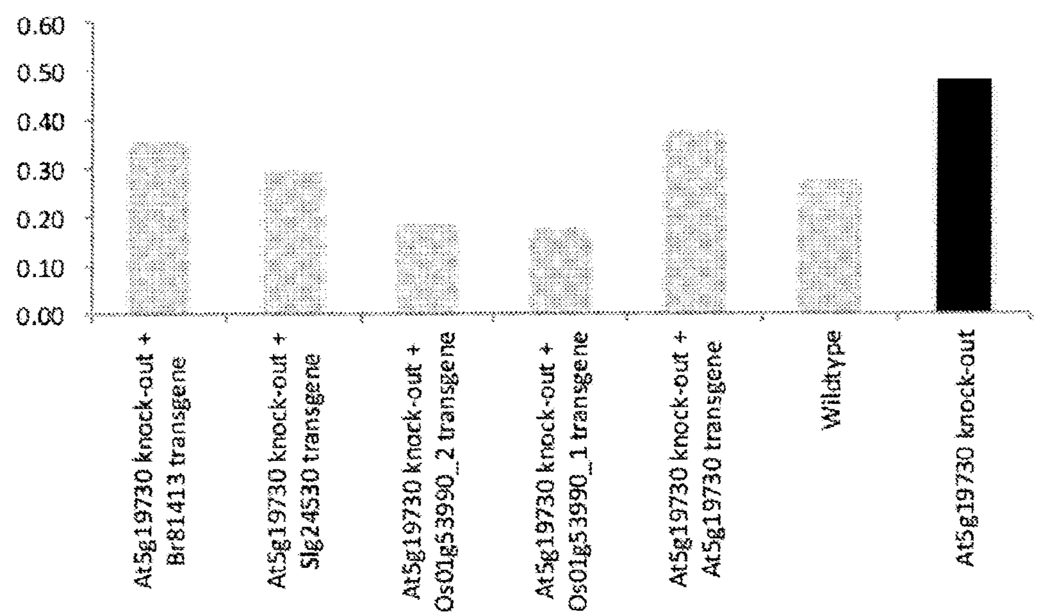
FIG. 3 shows drought survival of an *Arabidopsis* At5g19730 insertion mutant (pectinesterase knockout). The *Arabidopsis* At5g19730 insertion mutant survived drought significantly better ($p<0.05$) than wild-type plants or At5g19730 insertion mutants complemented with homologs from *Brassica rapa, Solanum lycopersicum*, or *Oryza sativa*. This figure demonstrates not only that an insertion mutation in this gene provides a drought resistant phenotype, but also that homologs of this gene from evolutionary distinct monocot and dicot species operate to restore the normal drought-susceptible phenotype. Gray bars have significantly lower values ($p<0.05$) than black bars.

FIG. 2 shows the drought resistant phenotype (At5g19730 KO) versus the drought sensitive phenotype (Wild-type). FIG. 3 shows drought survival of an *Arabidopsis* At5g19730 insertion mutant (pectinesterase knockout). The *Arabidopsis* At5g19730 insertion mutant survived drought significantly better ($p<0.05$) than wild-type plants or At5g19730 insertion mutants complemented with homologs from *Brassica rapa* ("Br81413 transgene"), *Solanum lycopersicum* ("SIg24530 transgene"), or *Oryza sativa* ("Os01g53990_1 transgene" and "Os01g53990_2 transgene"). This figure demonstrates not only that an insertion mutation in this gene provides a drought resistant phenotype, but also that homologs of this gene from evolutionary distinct monocot (*Oryza sativa*) and dicot species (*Arabidopsis thaliana, Brassica rapa, Solanum lycopersicum*) operate to restore the normal drought-susceptible phenotype. Gray bars have significantly lower values ($p<0.05$) than black bars.

The invention claimed is:

1. A method of producing a plant having improved drought tolerance, the method comprising:

(a) reducing the endogenous expression of a gene encoding SEQ ID NO: 4, 6, 8, or 10 in a plant protoplast or plant cell, wherein the expression is reduced by introducing a mutation into the endogenous gene or by introducing into said plant a silencing construct that targets the endogenous gene;

(b) regenerating a plant from the plant protoplast or plant cell; and (c) selecting a plant for increased drought tolerance.

2. The method according to claim 1, wherein the plant is *Brassica rapa* and the endogenous gene comprises SEQ ID NO: 3.

3. The method according to claim 1, wherein the plant is *Solanum lycopersicum* and the endogenous gene comprises SEQ ID NO: 5.

4. The method according to claim 1, wherein the plant is *Oryza sativa* and the endogenous gene comprises SEQ ID NO: 7.

5. The method according to claim 1, wherein the plant is *Oryza sativa* and the endogenous gene comprises SEQ ID NO: 9.

6. The method according to claim 1, the method further comprising producing a progeny plant or plant product from the selected plant.

* * * * *